(12) United States Patent
Andersen et al.

(10) Patent No.: US 8,323,897 B2
(45) Date of Patent: Dec. 4, 2012

(54) MULTIPLEX AMPLIFICATION OF POLYNUCLEOTIDES

(75) Inventors: Mark R. Andersen, San Mateo, CA (US); David W. Ruff, San Francisco, CA (US)

(73) Assignee: Applied Biosystems, LLC, Carlsbad, CA (US)

( * ) Notice: Subject to any disclaimer, the term of this patent is extended or adjusted under 35 U.S.C. 154(b) by 477 days.

(21) Appl. No.: 10/723,520

(22) Filed: Nov. 26, 2003

(65) Prior Publication Data

US 2004/0175733 A1 Sep. 9, 2004

Related U.S. Application Data

(60) Provisional application No. 60/431,156, filed on Dec. 4, 2002, provisional application No. 60/525,284, filed on Nov. 25, 2003.

(51) Int. Cl.
  *C12Q 1/68* (2006.01)
  *C12P 19/34* (2006.01)
(52) U.S. Cl. ..................... 435/6.12; 435/91.2
(58) Field of Classification Search .................. None
  See application file for complete search history.

(56) References Cited

U.S. PATENT DOCUMENTS

| | | | |
|---|---|---|---|
| 4,683,195 A | 7/1987 | Mullis et al. | |
| 4,683,202 A | 7/1987 | Mullis | |
| 4,965,188 A | 10/1990 | Mullis et al. | |
| 5,035,996 A | 7/1991 | Hartley | |
| 5,130,238 A | 7/1992 | Malek et al. | |
| 5,298,392 A | 3/1994 | Atlas et al. | |
| 5,354,668 A | 10/1994 | Auerbach | |
| 5,422,252 A | 6/1995 | Walker et al. | |
| 5,427,930 A | 6/1995 | Birkenmeyer et al. | |
| 5,437,976 A | 8/1995 | Utermohlen | |
| 5,455,166 A | 10/1995 | Walker | |
| 5,512,430 A | 4/1996 | Gong | |
| 5,538,848 A | 7/1996 | Livak et al. | |
| 5,582,989 A | 12/1996 | Caskey et al. | |
| 5,593,838 A | 1/1997 | Zanzucchi et al. | |
| 5,612,473 A | 3/1997 | Wu et al. | |
| 5,624,825 A | 4/1997 | Walker et al. | |
| 5,705,365 A | 1/1998 | Ryder et al. | |
| 5,716,784 A | 2/1998 | Di Cesare et al. | |
| 5,723,591 A | 3/1998 | Livak et al. | |
| 5,728,526 A | 3/1998 | George, Jr. et al. | |
| 5,736,365 A | 4/1998 | Walker et al. | |
| 5,738,995 A | 4/1998 | Wu et al. | |
| 5,750,338 A | 5/1998 | Collin et al. | |
| 5,776,682 A * | 7/1998 | First et al. ............... | 435/6 |
| 5,843,660 A | 12/1998 | Schumm et al. | |
| 5,882,856 A | 3/1999 | Shuber et al. | |
| 5,888,736 A | 3/1999 | Lacroix et al. | |
| 5,912,148 A | 6/1999 | Eggerding | |
| 5,952,173 A | 9/1999 | Hansmann et al. | |
| 5,955,268 A | 9/1999 | Granados | |
| 5,981,180 A | 11/1999 | Chandler et al. | |
| 5,989,809 A | 11/1999 | Stavrianopoulos | |
| 6,001,571 A | 12/1999 | Mandecki | |
| 6,013,440 A | 1/2000 | Lipshutz et al. | |
| 6,090,558 A | 7/2000 | Butler et al. | |
| 6,153,425 A | 11/2000 | Kozwich et al. | |
| 6,207,372 B1 | 3/2001 | Shuber | |
| 6,270,967 B1 | 8/2001 | Whitcombe et al. | |
| 6,403,303 B1 | 6/2002 | Shipman et al. | |
| 6,440,661 B1 | 8/2002 | Ogreid et al. | |
| 6,472,156 B1 * | 10/2002 | Wittwer et al. ................ | 435/6 |
| 6,605,451 B1 | 8/2003 | Marmaro et al. | |
| 6,618,679 B2 | 9/2003 | Loehrlein et al. | |
| 7,118,910 B2 * | 10/2006 | Unger et al. ............... | 435/288.5 |
| 7,531,328 B2 | 5/2009 | Gerdes et al. | |
| 2002/0182622 A1 | 12/2002 | Nakamura et al. | |
| 2003/0186246 A1 * | 10/2003 | Willey et al. .............. | 435/6 |
| 2004/0146897 A1 * | 7/2004 | Park et al. ................ | 435/6 |
| 2005/0048531 A1 | 3/2005 | Mittman et al. | |
| 2005/0175987 A1 * | 8/2005 | Jansen et al. ............. | 435/5 |

FOREIGN PATENT DOCUMENTS

| | | |
|---|---|---|
| EP | 320308 | 6/1989 |
| EP | 0 364 255 A2 | 4/1990 |
| EP | 00897990 | 2/1999 |
| EP | 1026258 | 8/2000 |
| JP | 2002539769 | 11/2002 |
| KR | 20020000280 | 6/2000 |
| WO | 97/19191 | 5/1997 |
| WO | 97/43441 | 11/1997 |
| WO | 98/24928 | 6/1998 |
| WO | 98/46797 | 10/1998 |
| WO | 99/64624 | 12/1999 |
| WO | 00/44935 | 8/2000 |
| WO | 01/32909 | 5/2001 |
| WO | WO 01/61033 | 8/2001 |
| WO | WO 01/61034 A1 | 8/2001 |
| WO | WO 01/94634 A2 | 12/2001 |
| WO | 02/090505 | 11/2002 |
| WO | 2004/051218 | 6/2004 |

OTHER PUBLICATIONS

Heid et al. (1996) Genome research 6:986-994.*
Dolganov et al. (2001) Genome research 11: 1473-1483.*
Ohnishi et al. (2001) J. Hum Genet 46:471-477.*
Wang et al. (1998) Science 280: p. 1077-1082.*
Assays-by-Design[SM] Service [online]. [retrieved on May 13, 2003], Retrieved from the Applied Biosystems using Internet <URL: http://www.applied biosystems.com/products/productdetail.cfm?prod_id=761.>.
Assays-on-Demand™ Gene Expression Products [online], [retrieved on May 13, 2003, Retrieved from the Applied Biosystems using Internet <http://www.applied biosystems.com/products/productdetail.cfm?prod_id=1101>.
Assays-on-Demand™ SNP Genotyping Products [online], [retrieved on May 13, 2003], Retrieved from the Applied Biosystems using Internet <http://www.applied biosystems.com/products/productdetail.cfm?prod_id=1141>.

(Continued)

*Primary Examiner* — Gary Benzion
*Assistant Examiner* — David Thomas

(57) ABSTRACT

The present invention provides methods, reagents and kits for carrying out a variety of assays suitable for analyzing polynucleotides or samples that include an amplification step performed in a multiplex fashion. Also provided are methods for analyzing and improving the efficiency of amplification and for carrying out gene expression analysis.

12 Claims, 9 Drawing Sheets

OTHER PUBLICATIONS

Figure 1:
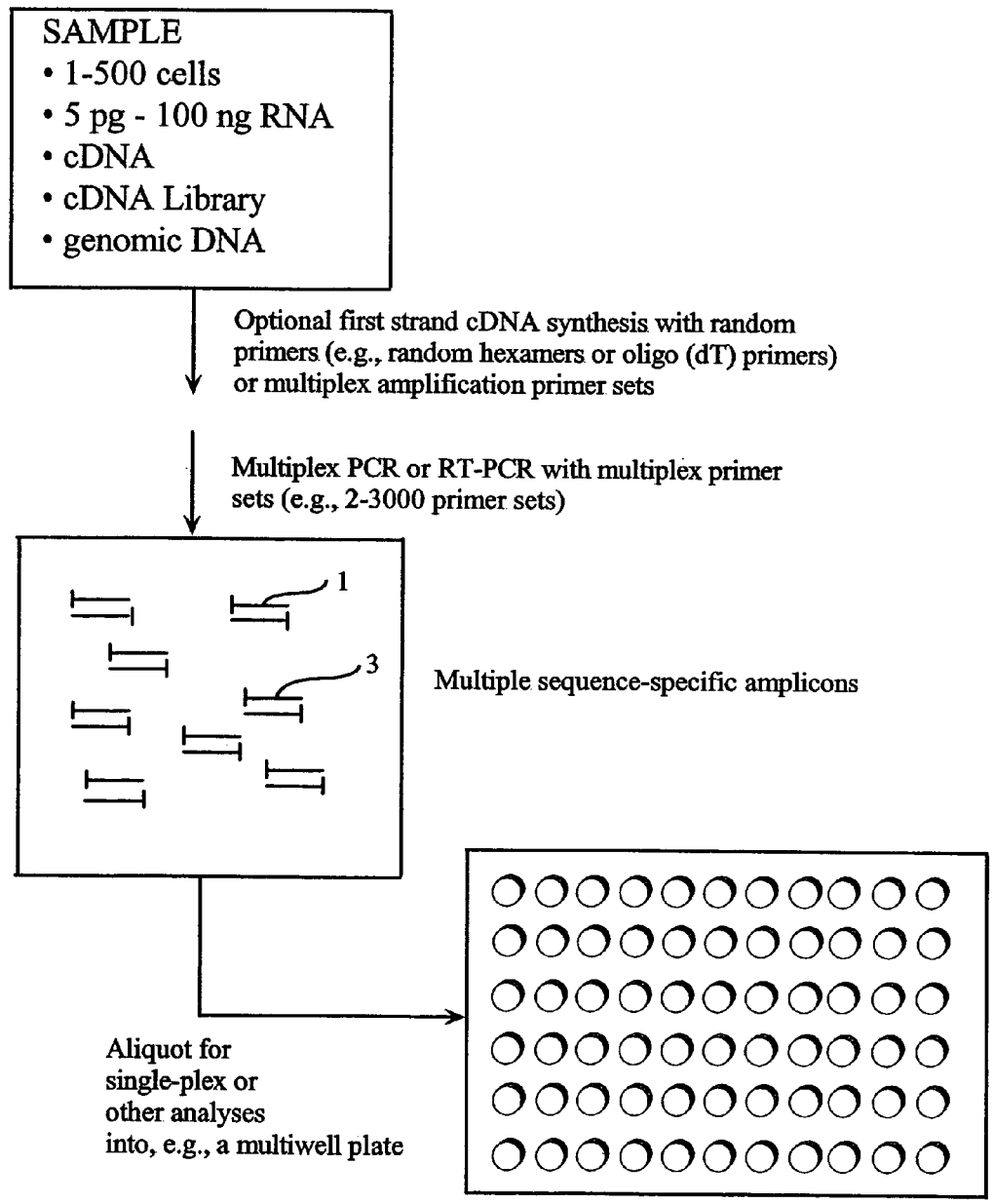

User Bulletin #2: ABI Prism 7700 Sequence Detection System. Subject: Relative Quantitation of Gene Expression, Datasheet. Applied Biosystems, 1997 (updated Oct. 2001).

Chamberlain, J.S.. "Deletion screening of the Duchenne muscular dystrophy locus via multiplex DNA amplification", *Nucleic Acids Research*, 1988, 16(23): 11141-11156.

Dolganov, G., "A Novel Method of Gene Transcript Profiling in Airway Biopsy Homogenates Reveals Increased Expression of a $Na^+$-$K^+$-$Cl^-$ Cotransporter (NKCC1) in Asthmatic Subjects", 2001, 11:1473-1483.

Edwards, M., et al., "Multiiplex PCR: Advantages, Development, and Applications", *PCR Methods and Applications*, Cold Spring Harbor Laboratory, 1994, pp. S65-S75.

Exner, M., et al., "Sensitivity of multiplex real-time PCR reactions, using the LightCycler and the ABI PRISM 7700 Sequence Detection System, is dependent on the concentration of the DNA polymerase", *Mol. Cell Probes*, Oct. 2002, 16:351-357.

Henegariu, O., "Multiplex PCR: Critical Parameters and Step-by-Step Protocor", *BioTechniques*, Sep. 1997, 23:504-511.

Jayaraman, K., et al., "A PCR-Mediated Gene Synthesis Strategy Involving the Assembly of Oligonucleotides Representing Only One of the Strands", *BioTechniques*, 1992, 12(3): 392-398.

Li, D., et al., "Multiplex co-amplification of 24 retinoblastoma gene exons after pre-amplification by long-distance PCR". *Nucleic Acids Research*, 1996, 24(3): 538-539.

Peirson, S.N., "Experimental validation of novel and conventional approaches to quantitative real-time PCR data analysis", *Nucleic Acids Res.*, 2003, 31(14):e73.

Shuber, A., et al., "A Simplified Procedure for Developing Multiplex PCRs", *Genome Research*, 1995, 5: 488-493.

Tichopad, A., et al., "Standardized determination of real-time PCR efficiency from a single reaction set-up", *Nucleic Acids Res.*, 2003, 31:e122.

C.T. Wittwer et al., "The LightCycler™: A Microvolume Multisample Fluorimeter with Rapid Temperature Control", BioTechniques 22, vol. 22, No. 1 (1997); 176-181.

Supplementary European Search Report dated Jun. 30, 2006 issued in EP Application No. 03796461.1, 5 pgs.

K. Rudi et al., "A Novel Multiplex Quantitative DNA Array Based PCR (MQDA-PCR) for Quantification of Transgenic Maize in Food and Feed" Nucleic Acids Research, 2003, vol. 31, No. 11 e62, pp. 1-8.

Bej, A K. et al., "Detection of Coliform Bacteria in Water by Polymerase Chain Reaction and Gene Probes", *Applied and Environmental Microbiology*, vol. 56, No. 2, Feb. 1990, 307-314.

Bej, A. K. et al., "Detection of Coliform Bacteria and *Escherichia Coli* by Multiplex Polymerase Chain Reaction: Comparison With Defined Substrate and Plating Methods for Water Quality Monitoring", *Applied and Environmental Microbiology*, vol. 57, No. 8, Aug. 1991, 2429-2432.

Bej, A. K. et al., "Detection of *Escherichia coli* and *Shigella* spp. In Water by Using the Polymerase Chain Reaction and Gene Probes for uid", *Applied and Environmental Microbiology*, vol. 57, No. 4, Apr. 1991, 1013-1017.

Bej, A. K. et al., "Multiplex PCR Amplification and Immobilized Capture Probes for Detection of Bacterial Pathogenes and Indicators in Water", *Molecular and Cellular Probes*, vol. 4, Issue 5, Academic Press, London, GB, Oct. 1990, 353-365.

Borg, K. L. et al., "Detection of cytomegalovirus using 'boosted' nested PCR.", *Molecular and Cellular Probes*, vol. 9, No. 4, England, Aug. 1995, 251-257.

D'Aquila, Richard T. et al., "Maximizing sensitivity and specificity of PCR by pre-amplification heating", *Nucleic Acids Research*, vol. 19, No. 13, Oxford University Press, Jul. 11, 1991, 3749.

Gonin, P. et al., "Performance of a multiplex PCR for the determination of Haemophilus influenzae capsular types in the clinical microbiology laboratory", *Diagnostic Microbiology and Infectious Disease*, vol. 37, No. 1, US, May 2000, 1-4.

Graves, L. M. et al., "Universal Bacterial DNA Isolation Procedure", *Diagnostic Molecular Microbiology; Principles and Applications*, American Society for Microbiology, Washington, D.C., 1993, 617-621.

Green, D et al., "Detection of faecal pollution in water by an *Escherichia coli* uidA gene probe", *Journal of Microbiological Methods*, vol. 13, Issue 3, Jul. 1991, 207-214.

Henegariu, O et al al., "Multiplex PCR: Critical Parameters and Step-By-Step Protocol", *Biotechniques*, vol. 23, No. 3, Eaton Publishing, Natick, US, Sep. 1997, 504-511.

Kaltenboeck, "Two-Step Polymerase Chain Reactions and Restriction Endonuclease Analyses Detect and Differentiate ompA DNA of *Chlamydia* spp", *Journal of Clinical Microbiology*, vol. 30, No. 5, American Society for Microbiology, May 1992, 1098-1104.

Kato, K., "Laboratory Manual PCR—Study and Application to Clinical Diagnosis", *First Edition Takara Shuzo Co. Ltd*, 1996, 73-81.

Lin, Z et al., "Multiplex Genotype Determination at a Large Number of Gene Loci", *Proceedings of the National Academy of Sciences of the United States*, vol. 93, No. 6, Genetics, USA, Mar. 1996, 2582-2587.

Liu, Q, "Subcycling-PCR for Multiplex Long-Distance Amplification of Regions with High and Low GC Content: Application to the Inversion Hotspot in the Factor VIII Gene", *Bio Techniques*, vol. 25, No. 6, Dec. 1998, 1022-1028.

Longo, M et al., "Use of uracil DNA glycosylase to control carry-over contamination in polymerase chain reactions", *Gene*, vol. 93, 1990, 125-128.

Lupo, M et al., "Gene Controlling L-Glutamic Acid Decarboxylase Synthesis in *Escherichia coli* K-12", *Journal of Bacteriology*, vol. 103, No. 2, American Society for Microbiology, USA, Aug. 1970, 382-386.

Martell, M et al., "High-Throughput Real-Time Reverse Transcription-PCR Quantitation of Hepatitis C Virus RNA", *Journal of Clinical Microbiology*, vol. 37, No. 2, American Society for Microbiology, Feb. 1999, 327-332.

Min, J. et al., "Highly Sensitive and Specific Detection of Viable *Escherichia coli* in Drinking Water", *Analytical Biochemistry*, vol. 303, Issue 2, Elsevier Science, USA, Apr. 15, 2002, 186-193.

Picard, C. et al., "Detection and Enumeration of Bacteria in Soil by Direct DNA Extraction and Polymerase Chain Reaction", *Applied and Environmental Microbiology*, vol. 58, No. 9, Sep. 1992, 2717-2722.

Rice, et al., "Detection of *Escherichia coli* in Water Using a Colorimetric Gene Probe Assay", *Journal of Environmental Science and Health*, vol. 30, Issue 5, 1995, 1059-1067.

Ruano, G et al., "Coupled amplification and sequencing of genomic DNA", *Proceedings of the National Academy of Sciences of the United States of America*, vol. 88, 1991, 2815-2519.

Ruano, G. et al., "Biphasic Amplification of Very Dilute DNA Samples Via 'Booster' PCR", *Nucleic Acids Research*, vol. 17, No. 13, Oxford University Press, Surrey, GB, Jul. 11, 1989, 5407.

Ruano, G. et al., "Booster PCR: A Biphasic Paradigm for Amplification of a Few Molecules of Target", *Amplifications: A Forum for PCR Users*, Perkin-Elmer Co., Norwalk, CT, US, Sep. 1989, 12-13.

Saiki, R. K., "The Design and Optimization of the PCR", *PCR Technology. Principles and Applications for DNA Amplification*, Stockton Press, New York, US, Jan. 1989, 7-16.

Saulnier, P. et al., "Detection of Genes in Feces by Booster Polymerase Chain Reaction", *Journal of Clinical Microbiology*, vol. 30, No. 8, American Society for Microbiology, Aug. 1992, 2080-2083.

Sheridan, G. E. et al., "Detection of mRNA by Reverse Transcription-PCR as an Indicator of Viability in *Escherichia coli* Cells", *Applied and Environmental Microbiology*, vol. 64, No. 4, American Society for Microbiology, Apr. 1998, 1313-1318.

Song, Y. et al., "Rapid identification of 11 human intestinal Lactobacillus species by multiplex PCR assays using group- and species-specific primers derived from the 16S-23S rRNA intergenic spacer region and its flanking 23S rRNA", *FEMS Microbiology Letters*, vol. 187, No. 2, Federation of European Microbiological Societies, Elsevier Science B.V., Netherlands, 2000, 167-173.

Tettelin, et al., "Optimized Multiplex PCR: Efficiently Closing a Whole-Genome Shotgun Sequencing Project", *Genomics*, vol. 62, 1999, 500-507.

Waters, L. C. et al., "Microchip Device for Cell Lysis, Multiplex PCR Amplification, and Electrophoretic Sizing", *Analytical Chemistry*, vol. 70, No. 1, American Chemical Society, Columbus, US, 1998, 158-162.

Wittwer, C. et al., "Real-Time Multiplex PCR Assays", Methods, vol. 25, Elsevier Science, USA, 2001, 430-442.

* cited by examiner

MULTIPLEX AMPLIFICATION OF POLYNUCLEOTIDES

1. CROSS-REFERENCE TO RELATED CO-PENDING APPLICATIONS

This application claims benefit of priority under 35 U.S.C. §119(e) to application No. 60/431,156, Dec. 4, 2002 and application No. 60/525,284, entitled "MULTIPLEX AMPLIFICATION OF POLYNUCLEOTIDES," filed Nov. 25, 2003, the disclosure of which is incorporated herein by reference.

2. FIELD OF THE INVENTION

The present invention relates to the field of molecular biology, and in particular provides methods, reagents and kits for amplifying polynucleotide sequences of interest in a multiplex fashion. Once amplified, the multiplex amplification product can be used in downstream analyses without further purification or manipulation.

3. BACKGROUND OF THE INVENTION

The general principles and conditions for amplification of nucleic acids using polymerase chain reaction are well known in the art (e.g., U.S. Pat. Nos. 4,683,195; 4,683,202; and 4,965,188). Amplification of nucleic acids from tissue samples represents an invaluable resource for both diagnosis and prognosis determinations, as well as the ability to correlate disease states with genetic disorders, including single nucleotide polymorphisms (SNPs), aberrant gene expression, chromosomal and gene rearrangement, translocation and/or alternate splicing, and chromosomal duplication/elimination. However, conventional polymerase chain reaction methods allow for the amplification of only a single DNA target species per PCR reaction (e.g., singe-plex PCR). For example, the amplification of 10,000 target sequences of interest would typically require 10,000 separate polymerase chain reactions based on conventional PCR procedures. The conventional approaches prove both time consuming and costly. There is, accordingly, a need in the art for improved methods of amplifying target sequences from a sample wherein any plurality of target sequences may be amplified simultaneously under identical reaction conditions in a multiplex fashion.

Moreover, certain downstream assays, such as array-based assays and quantitative PCR assays require a significantly high quantity of starting sample of target nucleic acid for carrying out the appropriate analyses. In situations where only a limited quantity of starting sample is available for use, only one or a few downstream analyses may be performed before the sample is depleted. There is, accordingly, a need in the art for methods which amplify, or significantly increase, the quantity of the starting material for permitting a variety of downstream assays to be carried out, optionally simultaneously, for providing a variety of information about a sample of interest in a relatively brief period of time.

4. SUMMARY OF INVENTION

In various embodiments, the present invention provides methods, reagents and kits for amplifying polynucleotide sequences of interest in a multiplex fashion. According to one embodiment of the methods of the invention, one or more polynucleotides are amplified, for example by the polymerase chain reaction ("PCR") or reverse-transcription polymerase chain reaction ("RT-PCR"), using a plurality of amplification primer pairs or sets, each of which is suitable or operative for amplifying a different polynucleotide sequence of interest. Unlike conventional amplification reactions, which are carried out with a single pair or set of amplification primers, and therefore generate a single amplified sequence ("amplicon"), by virtue of utilizing a plurality of amplification primer pairs or sets, the multiplex amplification methods of the invention permit the simultaneous amplification of a plurality of different sequences of interest in a single reaction.

As will be discussed in more detail, below, because a plurality of different sequences are amplified simultaneously in a single reaction, the multiplex amplifications may be used in a variety of contexts to effectively increase the concentration or quantity of a sample available for downstream analyses and/or assays. Once the sample has been multiplex amplified according to the methods described herein, it may be divided into aliquots, with or without prior dilution, for subsequent analyses. Owing to its increased concentration and quantity, significantly more analyses or assays can be performed with the multiplex amplified sample than could have been performed with the original sample. In many embodiments, multiplex amplification even permits the ability to perform assays or analyses that require more sample, or a higher concentration of sample, than was originally available. For example, after a 1000× multiplex amplification, subsequent assays could then be performed at 1000× less sample volume. Concentrating by multiplex amplification can also be used to dilute out amplification inhibitors that may be present in the original sample.

Although the multiplex amplification reactions may be carried out using conventional PCR reagents, reaction conditions and cycle temperatures and times, it has been discovered that the amounts of the various amplicons generated in the multiplex amplification reaction can be increased by increasing the amount or concentration of DNA polymerase used and/or the length of the time or duration of the primer extension reaction per cycle.

In certain embodiments, in generating the multiplex amplification products, the relative concentrations of the various amplicons generated during the amplification can be maintained sufficiently for detecting changes in the relative concentrations by increasing the amount or concentration of DNA polymerase used and/or the length of the time or duration of the primer extension reaction per cycle.

Moreover, while conventional primer concentrations can be used, it has been surprisingly discovered that the amplification proceeds with a high degree of efficiency in the presence of very low concentrations of amplification primers. By way of comparison, whereas conventional single-plex ("simplex") PCR amplifications are carried out in the presence of 300-900 nM each primer, highly efficient multiplex amplification was achieved with only 45 nM of each primer.

Both DNA and RNA target polynucleotides can be multiplex amplified using such low primer concentrations. Specifically, the reverse transcription of RNA into cDNA via a reverse-transcription and subsequent multiplex amplification of the resultant cDNA with a DNA polymerase may be accomplished using primers at low concentrations (e.g., 45 nM for each primer). Accordingly, the invention permits the amplification of both DNA and RNA target polynucleotides in a multiplex fashion using principles of conventional polymerase chain reactions (PCR) and reverse-transcription polymerase chain reactions (RT-PCR), respectively.

In addition, the individual primer concentrations do not need to be optimized; it has been discovered that using all primers at approximately equimolar concentrations yields good results. It was, moreover, demonstrated in particular embodiments of the invention that the use of low primer concentrations reduces the possibility of non-specific primer interactions (e.g., primer dimerization), thereby eliminating the need for optimization. The concentrations of primers described in various embodiments of the invention (e.g., 45 nM, each primer) were demonstrated to be sufficiently high to permit the multiplex amplification of target sequences yet low enough to prevent or avoid the primers from interacting non-specifically with one another. Thus, multiplex amplification of virtually any combination of sequences can be rapidly achieved without time-consuming optimization steps.

It has also been discovered that the presence of oligonucleotide probes in the multiplex amplification does not significantly interfere with the amplification reactions. Thus, the multiplex amplification can be effectively carried out in the presence of oligonucleotide probes, such as, for example, non-priming oligonucleotide probes designed for quantitative or real-time PCR analysis. Non-limiting examples of types of probes that can be present in the multiplex amplification include TAQMAN® probes (see, e.g., U.S. Pat. No. 5,538,848), stem-loop or hairpin MOLECULAR BEACONS™ (see, e.g., U.S. Pat. Nos. 6,103,476 and 5,925,517 and Tyagi & Kramer, 1996, Nature Biotechnology 14:303-308), stemless or linear beacons (see, e.g., WO 99/21881), PNA Molecular Beacons (see, e.g., U.S. Pat. Nos. 6,355,421 and 6,593,091), linear PNA beacons (see, e.g., Kubista et al., 2001, SPIE 4264:53-58), non-FRET probes (see, e.g., U.S. Pat. No. 6,150,097), SUNRISE®/AMPLIFLUOR® probes (U.S. Pat. No. 6,548,250), stem-loop and duplex SCORPION™ probes (Solinas et al., 2001, Nucleic Acids res. 29: E96 and U.S. Pat. No. 6,589,743), bulge loop probes (U.S. Pat. No. 6,590,091), pseudo knot probes (U.S. Pat. No. 6,548,250), cyclicons (U.S. Pat. No. 6,383,752), MGB ECLIPSE™ probe (Epoch Biosciences), hairpin probes (U.S. Pat. No. 6,596,490), peptide nucleic acid (PNA) light-up probes, self-assembled nanoparticle probes, and ferrocene-modified probes.

This discovery is significant, as it permits the ability to carry out multiplex amplification reactions using off-the-shelf commercially available reagents, such as the gene expression and SNP reagents sold under the tradename Assays-On-Demand® by Applied Biosystems (an Applera Corporation business; Foster City, Calif.). In this context, off-the-shelf reagents comprising amplification primers and probes can be pooled together and used in a multiplex amplification reaction without prior removal of probes. Like multiplex amplifications carried out in the absence of such oligonucleotide probes, multiplex amplifications carried out in the presence of such oligonucleotide probes can be divided into aliquots, with or without prior dilution, for subsequent analysis without further purification or manipulation.

Samples amplified in a multiplex fashion may be used in virtually any subsequent analysis or assay without further purification or manipulation. For example, the product of the multiplex amplification may be used for single polynucleotide polymorphism ("SNP") analysis, genotyping analysis, gene expression analysis, fingerprinting analysis, analysis of gene mutations for genetic diagnoses, analysis of rare expressed genes in cells, nucleic acid sequencing (e.g., U.S. Pat. No. 6,428,986), nucleic acid mini-sequencing (e.g., U.S. Pat. No. 6,479,242), and for hybridizing to arrays (e.g., U.S. Pat. No. 6,485,944). The multiplex amplification product is even suitable for further amplification analyses, such as analysis via quantitative or real-time PCR amplification. In this latter embodiment, the sequences of the primers used for the subsequent quantitative or real-time PCR analyses can be the same as or different from those employed in the initial multiplex amplification. The multiplex amplification product can be divided into aliquots each of which can be subject to subsequent single-plex or multiplex assays or analyses. Alternatively, the multiplex amplification product need not divided into aliquots, and various assays and analyses can be performed directly on the product.

Significantly, such subsequent analyses or assays can be carried out directly with the multiplex amplification product without having to first remove the pooled oligonucleotide probes and/or primers. Any probes and/or primers carried over into the subsequent analysis or assays will not interfere with the analysis or assay.

In yet another embodiment, the present invention provides a two-step method of analyzing a sample for the presence of one or more polynucleotide sequences of interest. In a first step, one or more polynucleotides derived from the sample (or a plurality of different samples) are multiplex amplified in the presence of a plurality of different amplification primer pairs or sets, as described above. In one embodiment, in a second step, the product of the multiplex amplification is single-plex amplified by polymerase chain reaction in the presence of a set of amplification primers operative or suitable for amplifying a sequence of interest and the single-plex amplification reaction monitored for accumulation of amplification product. In another embodiment, in a second step the multiplex amplification product is divided into a plurality of reaction vessels, the product in each vessel is single-plex amplified in the presence of a set of amplification primers operative or suitable for amplifying a sequence of interest and the single-plex amplifications monitored for the accumulation of amplification product. In either embodiment, the accumulation of single-plex amplification product indicates the sample contains the respective polynucleotide of interest.

The accumulation of single-plex amplification product can be monitored at the end of the reaction by conventional means, e.g., by chromatography, by eletrophoresis, by staining or by the use of a sequence specific hybridization probe (e.g., a fluorescently labeled probe). Alternatively, the accumulation of single-plex amplification product can be monitored as a function of time using well known methods, such as carrying out the single-plex amplification in the presence of one or more dyes or labels capable of producing a detectable signal upon binding double-stranded polynucleotide (e.g., SYBR® Green I or II, SYBR® Gold, ethidium bromide, or YO-PRO-1; Molecular Probes, Eugene, Oreg.) or an oligonucleotide probe labeled with a suitable labeling system (e.g. a TAQMAN® probe, or one of the various different types of exemplary probes described above).

The present invention also provides reagents and kits suitable for carrying out the multiplex amplifications and optional downstream analyses. In one embodiment, the kit includes a plurality of amplification primer sets suitable for carrying out a multiplex amplification packaged in a single container. The kit may optionally include one or more additional reagents for carrying out the amplification, such as a DNA polymerase enzyme, a reverse transcriptase enzyme and/or mixtures of nucleoside triphosphates ("dNTPs") suitable for extension of the primers via template-dependent DNA synthesis. The amount of optional polymerase included in the kit may be suitable for optimizing the efficiency of the multiplex amplification reaction. The various reagents may be packaged in combinations for maximal convenience, and may be modeled after the combinations of reagents available commercially for carrying out conventional PCR and/or RT-PCR amplification reactions (e.g., (2×) TAQMAN® Universal PCR Master Mix and TAQMAN® Gold RT-PCR Kit available from Applied Biosystems, an Applera Corporation business). The kit may further include reagents useful for carrying out downstream assays or analyses with the multiplex amplification product. For example, the kit may further include oligonucleotide probes useful for SNP detection or analysis, oligonucleotide microarrays, such as microarrays suitable for gene expression or SNP analyses, and/or "tailed" primers (see, e.g., Bengra et al., 2002, Clin, Chem. 48:2131-2140; Myakishev et al., 2001, Genome Res. 11:163-169; and U.S. Pat. No. 6,395,486) for universal amplification, detection and/or purification. In one embodiment, the kit further includes reagents suitable for carrying out a plurality of single-plex quantitative or real-time amplification reactions. Such reagents typically include a set of quantitative or real-time amplification primers, an oligonucleotide probe labeled with a labeling system suitable for monitoring the quantitative real-time amplification reaction, a DNA polymerase at a concentration suitable for single-plex amplification and/or mixtures of dNTPs suitable for template-dependent DNA synthesis. The kit may include one or more of any of these additional reagents.

Various embodiments of the multiplex amplification methods, reagents and kits of the present invention provide significant advantages to the state-of-the-art. For example, by virtue of the use of a plurality of amplification primers, some embodiments of the multiplex amplifications permit amplification of polynucleotide samples of limited quantity or copy number, thereby permitting, for the first time, the ability to perform one or more downstream analyses that would otherwise, owing to limitations of the sample quantity, be extremely difficult, time consuming, inaccurate or even unattainable. In certain embodiments, multiplex amplification can also permit target polynucleotide samples to be concentrated, even in instances where the original sample included a dilute pool of a plurality of target polynucleotides. Concentrating samples in this way enables the ability to perform downstream analyses and assays that require highly concentrated samples, even in instances where the original sample was too dilute. In further embodiments, multiplex amplifications can be performed in a single tube using off-the-shelf prepackaged reagents and permit the amplification of virtually any type of target polynucleotide sequence from virtually any type of sample, wherein reagents and reaction conditions need not be optimized to accommodate the amplification of a particular target sequence within a particular sample. In many embodiments, the multiplex amplifications described herein were found to proceed with a high degree of efficiency. The multiplex amplified product can therefore be used for downstream analyses where the relative or absolute quantities of copy numbers in the starting sample are assessed, such as, for example, expression profiling analyses. Other advantages of various embodiments of the present invention will be apparent upon review of the instant disclosure.

5. BRIEF DESCRIPTION OF THE DRAWINGS

Figure 2:
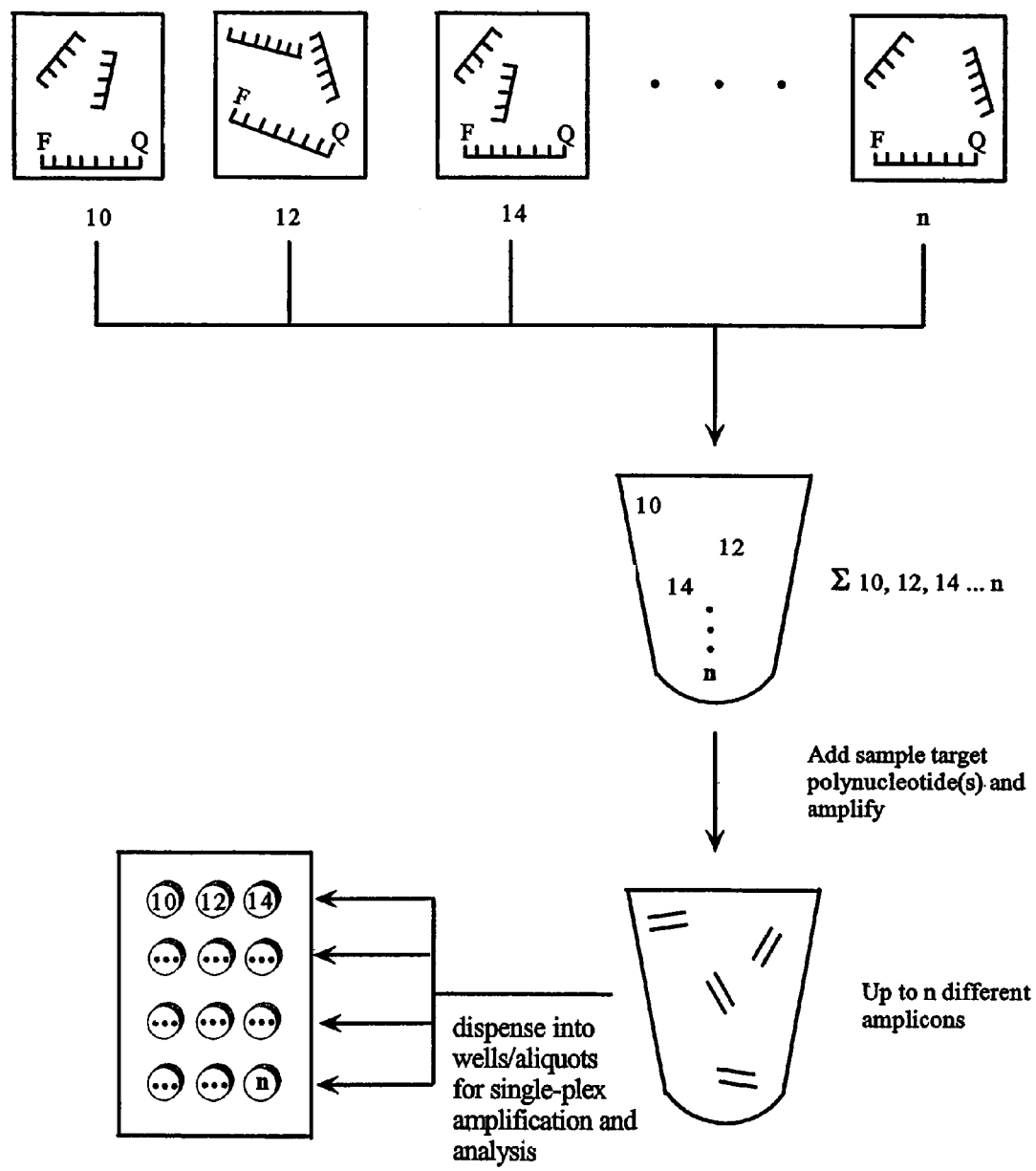
Figure 3:
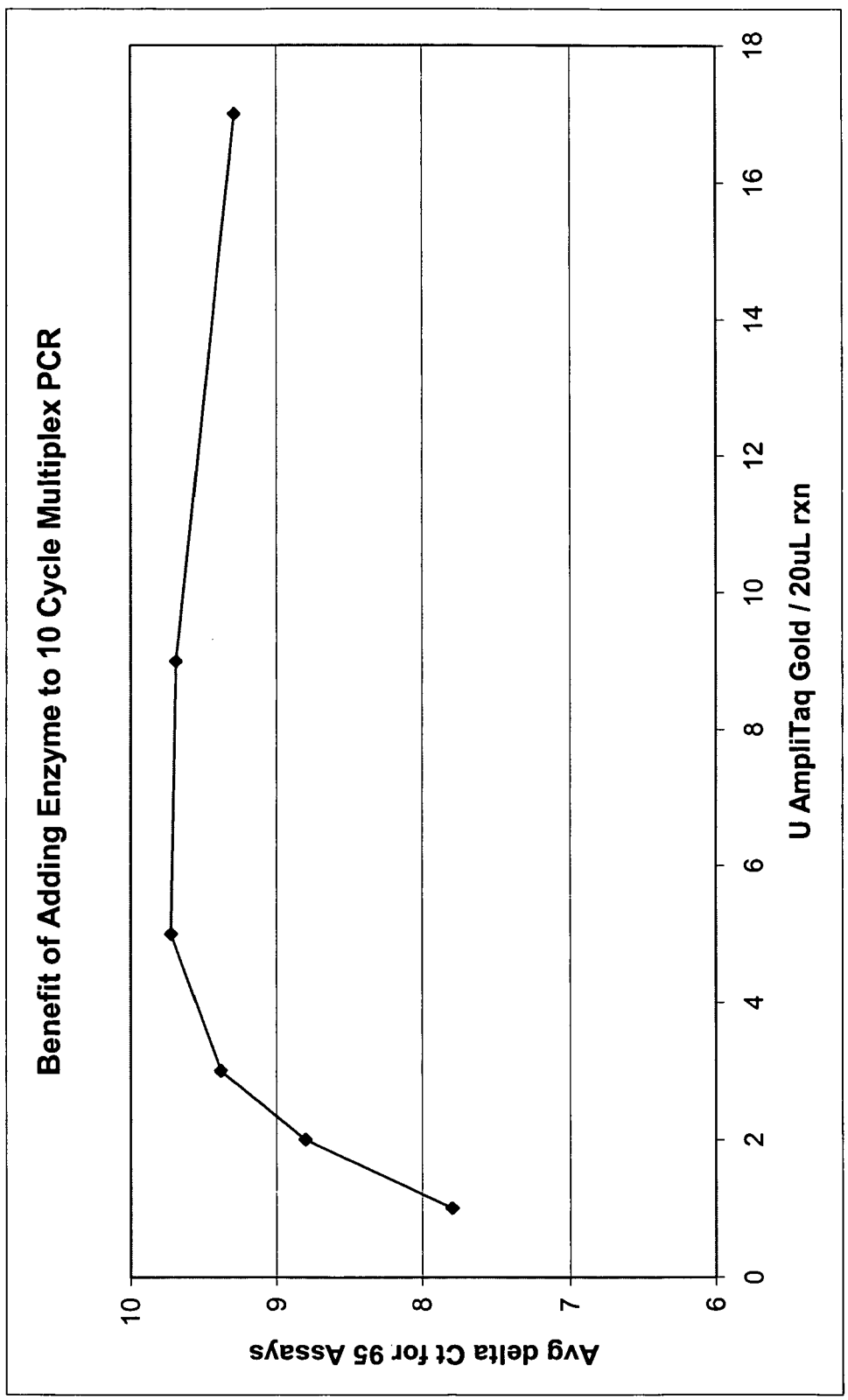
Figure 4:
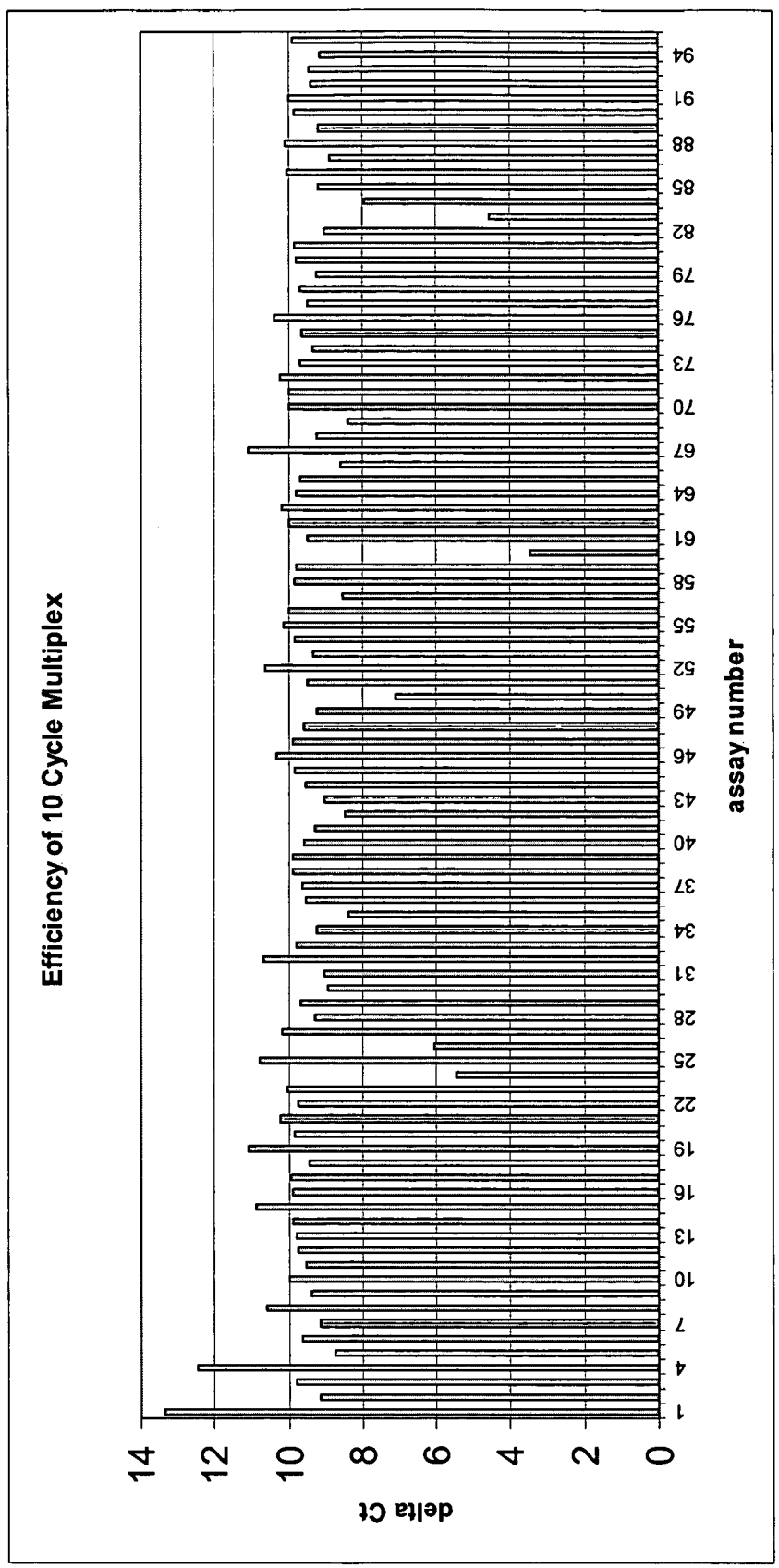
Figure 5:
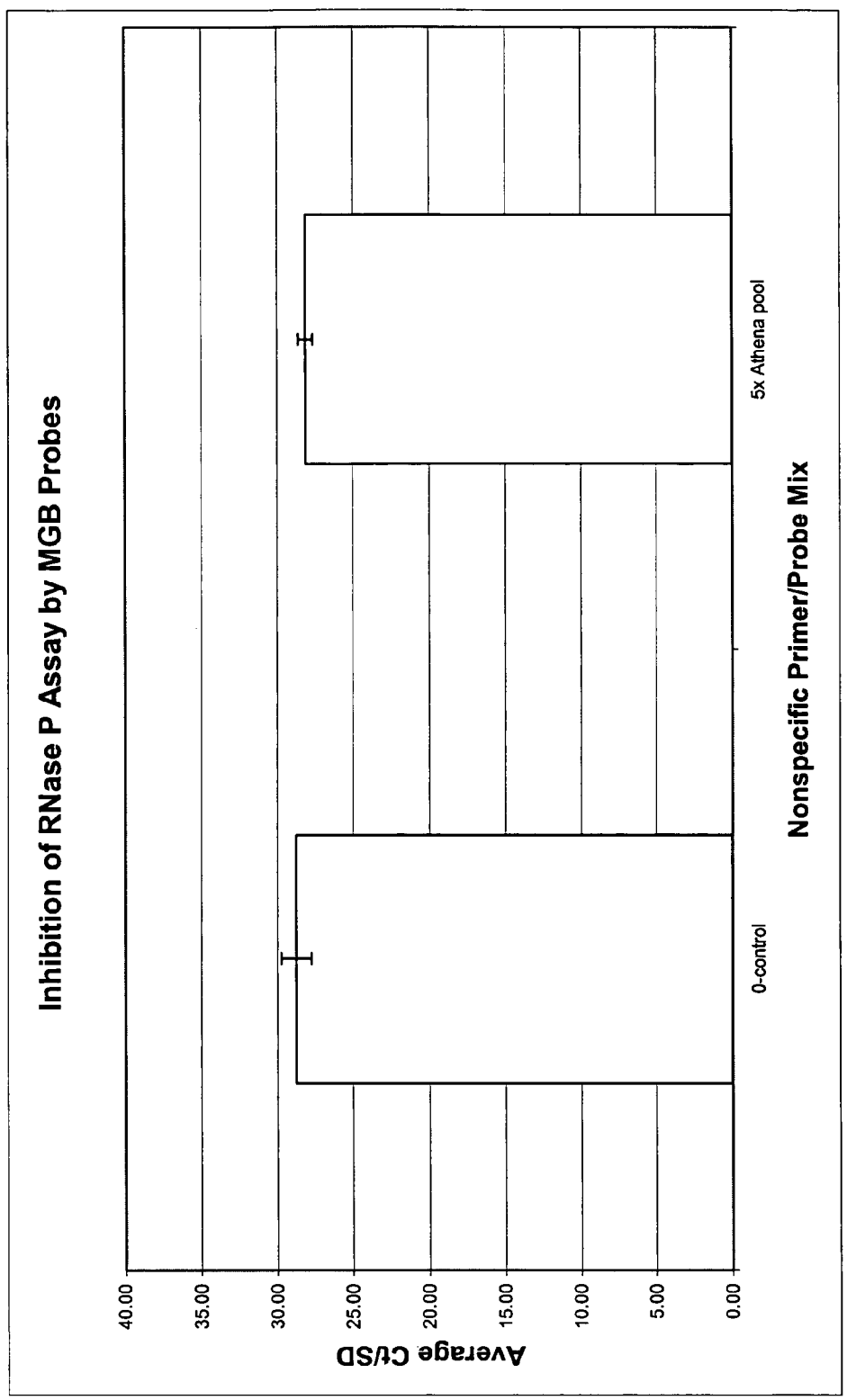
Figure 6:
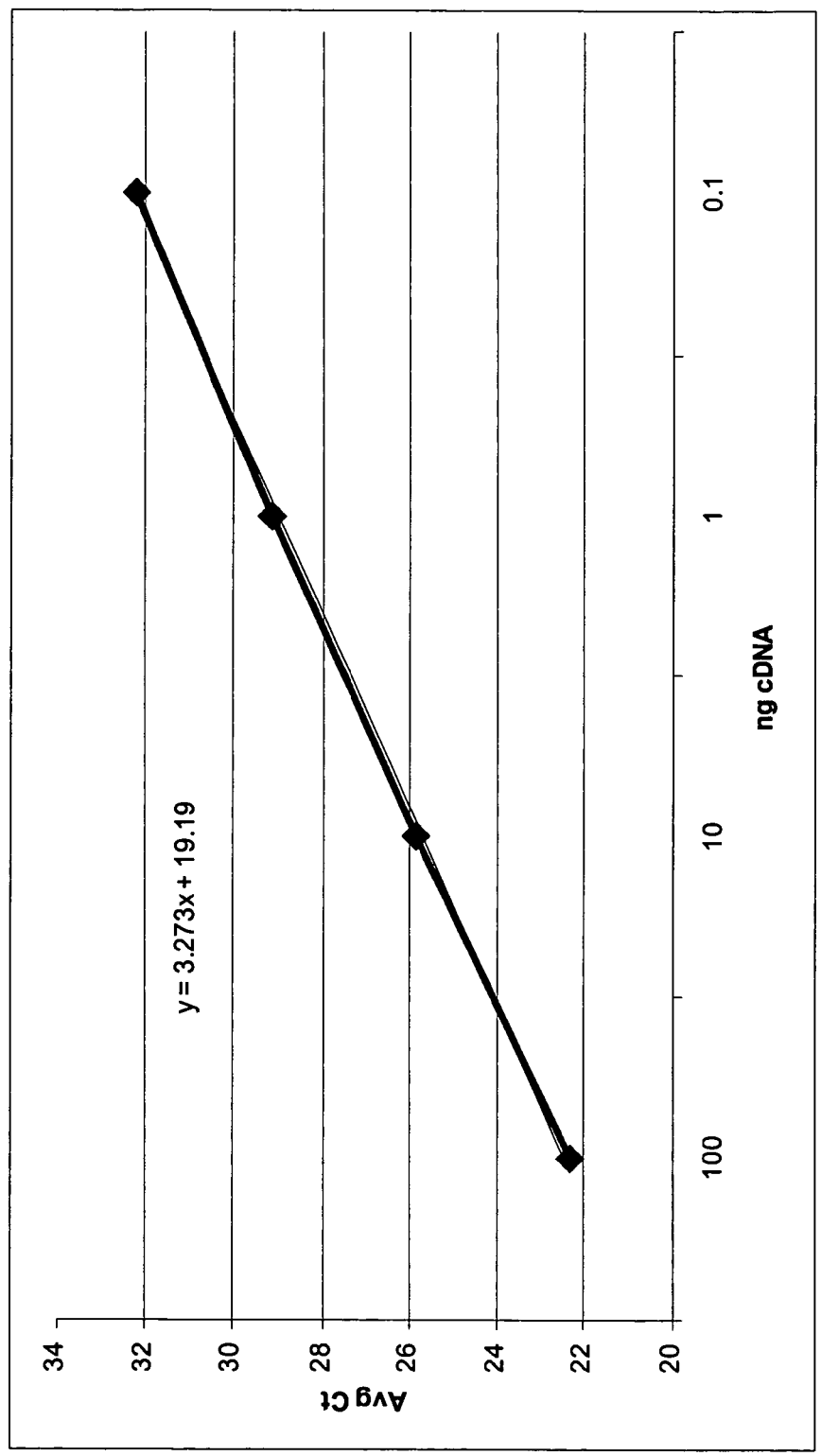
Figure 7:
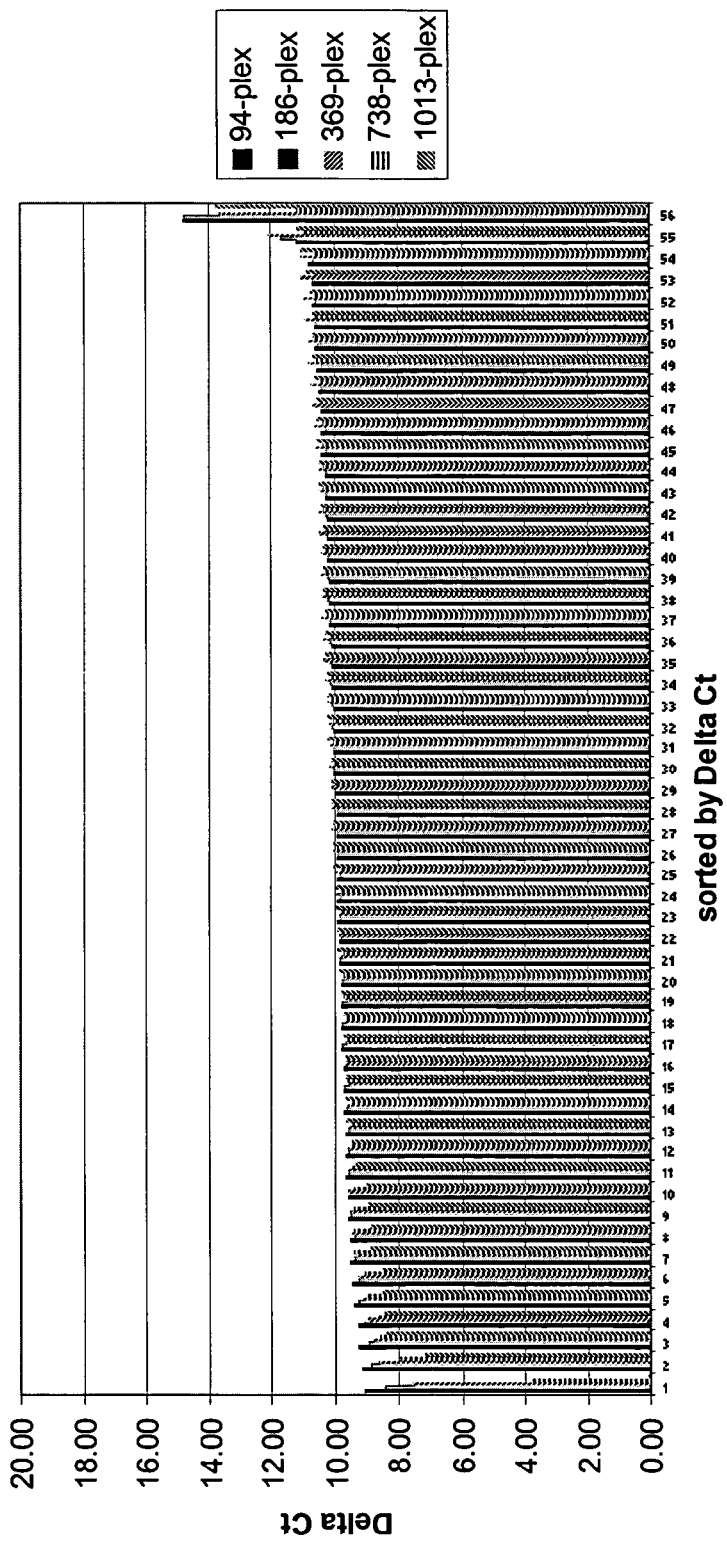
Figure 8:
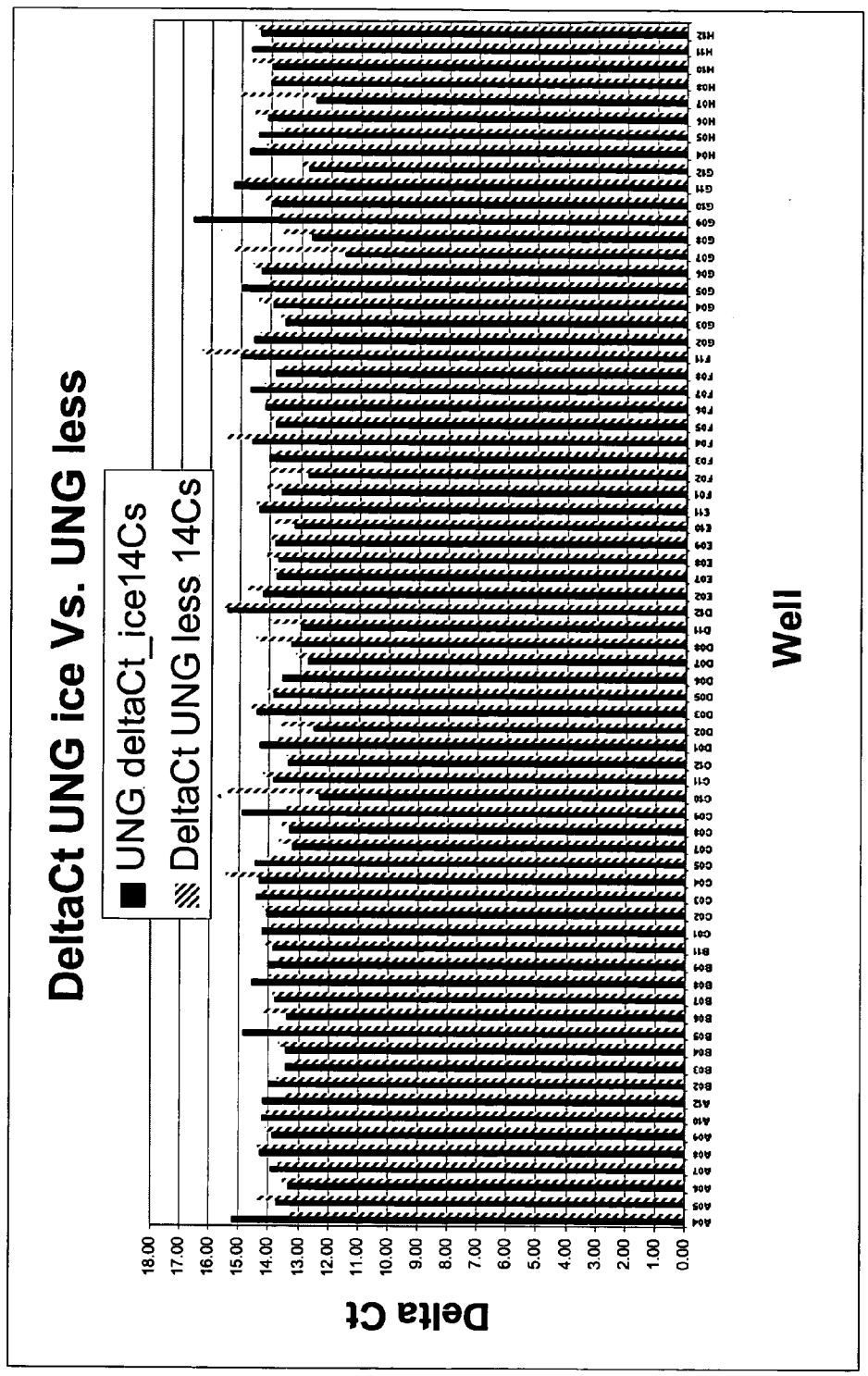
Figure 9:
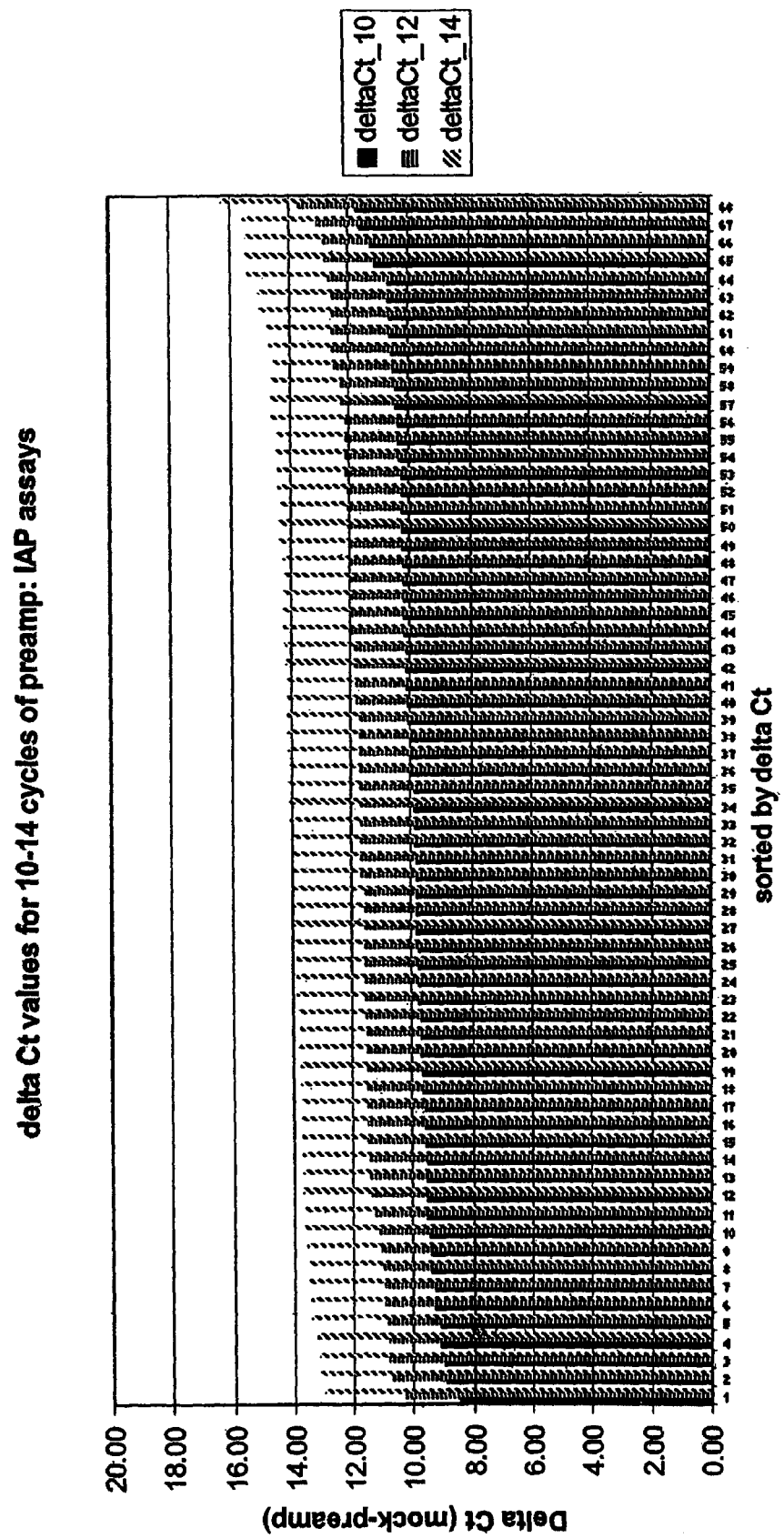

FIG. 1 provides a cartoon illustrating the general principles of an embodiment of a multiplex amplification according to the invention;

FIG. 2 provides a cartoon illustrating an embodiment of a two-step assay according to the invention in which a multiplex amplification is coupled with a plurality of downstream, single-plex ("simplex") quantitative or real-time PCR analyses;

FIG. 3 provides a graph illustrating the amplification efficiency of an embodiment of a 95-plex amplification reaction of the invention as a function of DNA polymerase concentration;

FIG. 4 provides a graph illustrating the observed amplification efficiency of an embodiment of a 95-plex amplification reaction of the invention carried out with a total of 100 ng cDNA (from a cDNA library) and 6 U/20 μL AMPLITAQ GOLD® for a total of 10 cycles (cycle time was approx. 1 min./cycle);

FIG. 5 provides a graph demonstrating that the presence of a plurality of amplification primers and oligonucleotide probes during an exemplary downstream single-plex assay does not detrimentally affect the performance of the assay;

FIG. 6 provides a graph demonstrating the linear relationship between amount of sample polynucleotide in a multiplex amplification and Ct value obtained during downstream individual real-time PCR amplifications;

FIG. 7 provides a bar graph illustrating the observed amplification efficiency of downstream single-plex assay amplifications after various multiplex amplifications;

FIG. 8 provides a bar graph illustrating the effect of UNG in a multiplex amplification on observed amplification efficiency of downstream single-plex assay amplifications; and FIG. 9 provides a graph illustrating the effect of increasing the number of PCR cycles in multiplex amplifications on the Ct values of downstream single-plex assay amplifications.

6. DETAILED DESCRIPTION

In certain embodiments, the present invention provides methods, reagents and kits for amplifying polynucleotide sequences of interest in a multiplex fashion. The multiplex amplifications utilize well-known principles and reagents for the amplification of DNA or RNA polynucleotides via the polymerase chain reaction ("PCR") or the reverse-transcription polymerase chain reaction ("RT-PCR"), respectively, with one important difference. Rather than using a single set or pair of amplification primers, the multiplex amplifications utilize a plurality of different amplification primer pairs or sets in a single reaction, permitting the simultaneous amplification of a plurality of polynucleotide sequences in a single reaction. Thus, rather than generating a single amplification product or "amplicon," the multiplex amplifications generate a plurality of different amplicons in a single reaction. As will be described in more detail below, polynucleotides that can be amplified in a multiplex fashion include both 2'-deoxyribonucleic acids (DNA) and ribonucleic acids (RNA). When the polynucleotide to be amplified ("target polynucleotide") is an RNA, it may be first reversed-transcribed to yield a cDNA, which can then be amplified in a multiplex fashion. Alternatively, the target RNA may be multiplex amplified directly in the presence of the plurality of amplification primer pairs using principles of RT-PCR. Accordingly, as used in the context of multiplex amplifications, "polymerase chain reaction" is meant to include both multiplex PCR and multiplex RT-PCR.

The principles of DNA amplification by PCR and RNA amplification by RT-PCR are well-known and described in myriad references, including: U.S. Pat. Nos. 4,683,195; 4,683,202; 4,800,159; 4,965,188; 5,338,671; 5,340,728; 5,405,774; 5,436,149; 5,512,462; 5,618,703; 6,037,129; 6,300,073; and 6,406,891; Innis et al., 1990, In: PCR Protocols A guide to Methods and Applications, Academic Press, San Diego; and Schlesser et al., 1991, Applied and Environ. Microbiol. 57:553-556, the disclosures of which are incorporated herein by reference. For ease of understanding the differences and advantages of the multiplex amplifications described herein, a brief summary of these amplification methods is provided. Conventional PCR requires at least two primers, a forward primer and a reverse primer, which hybridize to a double-stranded target polynucleotide sequence to be amplified. In PCR, a double-stranded target DNA polynucleotide which includes the sequence to be amplified is incubated in the presence of the two amplification primers, a DNA polymerase and a mixture of 2'-deoxyribonucleotide triphosphates ("dNTPs") suitable for DNA synthesis. To begin the amplification, the double-stranded target DNA polynucleotide is denatured and one primer is annealed to each strand of the denatured target. The primers anneal to the target DNA polynucleotide at sites removed from one another and in orientations such that the extension product of one primer, when separated from its complement, can hybridize to the other primer. Once a given primer hybridizes to its respective target DNA polynucleotide strand, the primer is extended by the action of the DNA polymerase. The extension product is then denatured from the target sequence, and the process is repeated. A PCR cycle (i.e. a thermocycle) typically includes the steps of denaturation, annealing and extension.

In successive cycles of this process, the extension products produced in earlier cycles serve as templates for subsequent DNA synthesis. Beginning in the second cycle, the product of the amplification begins to accumulate at a logarithmic rate. The final amplification product, or "amplicon," is a discrete double-stranded DNA molecule consisting of: (i) a first strand which includes the sequence of the first primer, which is followed by the sequence of interest, which is followed by a sequence complementary to that of the second primer, and (ii) a second strand which is complementary to the first strand.

Conventional RT-PCR permits the amplification of a target RNA polynucleotide sequence. In RT-PCR, a single-stranded RNA target which includes the sequence to be amplified (e.g., an mRNA) is incubated in the presence of a reverse transcriptase, two amplification primers, a DNA polymerase and a mixture of dNTPs suitable for DNA synthesis. One of the amplification primers anneals to the RNA target and is extended by the action of the reverse transcriptase, yielding an RNA/cDNA doubled-stranded hybrid. This hybrid is then denatured, and the other primer annealed to the denatured cDNA strand. Once hybridized, the primer is extended by the action of the DNA polymerase, yielding a double-stranded cDNA, which then serves as the double-stranded template or target for further amplification via conventional PCR, as described above. Thus, the main difference between conventional PCR and RT-PCR is the presence of the reverse-transcriptase in the reaction mixture of the latter. Following reverse transcription, the RNA can remain in the reaction mixture during subsequent PCR amplification, or it can be optionally degraded by well-known methods prior to subsequent PCR amplification.

A PCR and/or RT-PCR amplification can incorporate one or more of a variety of improvements as described in the art. Non-limiting example of such improvements include "hot start" PCR technique (D'Aquila et al., 1991, Nucl. Acids Res. 19:3749), "touchdown" PCR techniques (Don et al., 1991, Nucl. Acids Res. 19:4008), the use of polymerase enhancing factors (e.g. ArchaeMaxx™ available from Stratagene; see also U.S. Pat. No. 6,444,428) and the use of dUTP in place of dTTP with treatment by uracil N-glycosylase (UNG) (as described in Example 6 herein, and see U.S. Pat. No. 5,035, 996). Any of these improvements and/or other improvements for carrying out PCR and/or RT-PCR amplifications can be used in conjunction with the various methods described herein.

A general overview of certain embodiments of the invention is provided in FIG. 1. Referring to FIG. 1, one or more target polynucleotides from a sample, which may be one or more RNAs or DNAs, is amplified by PCR or RT-PCR in the presence of a plurality of amplification primer pairs, each of which is suitable for amplifying a different target sequence of interest. In some embodiments, the number of primer pairs can be at least 100, 300, 500, 1000, 10000, or 30000. As illustrated, when the sample or target polynucleotide is an RNA, the first cDNA strand may be optionally synthesized prior to multiplex amplification using either random RT-primers (e.g., random hexamers or oligo (dT) primers) or sequence-specific RT primers, as is well known in the art. Alternatively, the target RNA may be directly multiplex amplified by RT-PCR in the presence of the plurality of amplification primer pairs. Owing to the presence of the plurality of amplification primer pairs, the product of the multiplex amplification is a plurality of different amplicons, represented by amplicons 1 and 3.

As will be appreciated by skilled artisans, target polynucleotides suitable for multiplex amplification may be either DNA (e.g., cDNA or genomic DNA) or RNA (e.g., mRNA or rRNA) in nature, and may be derived or obtained from virtually any sample or source, wherein the sample may, optionally, be scarce or of a limited quantity. For example, the sample may be one or a few cells collected from a crime scene or a small amount of tissue collected via biopsy.

By way of example and not limitation, the target polynucleotide may be a chromosome or a gene or a portion or fragment thereof, a regulatory polynucleotide, a restriction fragment from, for example a plasmid or chromosomal DNA, genomic DNA, mitochondrial DNA, DNA from a construct or library of constructs (e.g., from a YAC, BAC or PAC library), RNA (e.g., mRNA, rRNA) or a cDNA or cDNA library. The target polynucleotide may include a single polynucleotide, from which a plurality of different sequences of interest may be amplified, or it may include a plurality of different polynucleotides, from which one or more different sequences of interest may be amplified. As will be recognized by skilled artisans, the sample or target polynucleotide may also include one or more polynucleotides that are not amplified in the multiplex amplification reaction.

An important embodiment of a multiplex amplification as described herein is its ability to amplify polynucleotide sequences from highly complex mixtures of sample polynucleotides. Indeed, many embodiments are suitable for multiplex amplification of target polynucleotide samples comprising tens, hundreds, thousands, hundreds of thousands or even millions of polynucleotide molecules. In specific embodiments, the multiplex amplification methods can be used to amplify pluralities of sequences from samples comprising cDNA libraries or total mRNA isolated or derived from biological samples, such as tissues and/or cells, wherein the cDNA, or alternatively mRNA, libraries may be quite large. For example, cDNA libraries or mRNA libraries constructed from several organisms, or from several different types of tissues or organs, can be multiplex amplified according to the methods described herein. As a specific example, multiplex amplification from an extremely complex library of cDNAs constructed from several different tissues or organs was achieved with good results (see, e.g., Example 4). It is believed that this particular cDNA library included in the range of 10,000-20,000 cDNAs.

The quantity of target polynucleotide amplified can vary widely. In many embodiments quantities suitable for conventional PCR and/or RT-PCR may be used. For example, the target polynucleotide may be from a single cell, from tens of cells, from hundreds of cells or even more, as is well known in the art. For many embodiments, including embodiments in which the target polynucleotide is a complex cDNA library, the total target polynucleotide may range from about 1 µg to 100 ng.

Skilled artisans will appreciate that several advantages flow from multiplex amplifications generally, and in particular multiplex amplifications carried out with complex target polynucleotides such as mRNA and/or cDNA libraries. First, samples including target polynucleotides that are present in low copy numbers can be effectively increased in quantity, permitting the ability to carry out significantly more downstream analyses or assays that would have been possible without multiplex amplification. Second, the multiplex amplification permits the ability to perform downstream analyses or assays that may not have been possible with the original sample owing to its limited quantity. Third, target polynucleotides within a large dilute pool or sample can be concentrated, permitting the ability to perform downstream analyses or assays requiring highly concentrated samples. Moreover, as will be described in more detail below in relation to certain embodiments, since the multiplex amplification proceeds with a high degree of efficiency, the relative concentrations of the various target sequences in the sample are sufficiently preserved to permit the ability to assess or quantify the relative concentrations in downstream analyses (e.g. in downstream gene expression profiling analyses).

The target polynucleotide(s) to be amplified can be prepared for multiplex amplification using conventional sample preparation techniques suitable for the type of amplification reaction to be used. For example, the polynucleotides may be isolated from their source via chromatography, precipitation, electrophoresis, as is well-known in the art. Alternatively, the polynucleotide(s) may be amplified directly from cells or from lysates of tissues or cells comprising the target polynucleotides. In some embodiments, the polynucleotide(s) to be amplified may be subjected to conventional sodium bisulphite treatment, or equivalent, in order to detect methylated cytosine residues (see, e.g., U.S. Pat. No. 6,596,488).

The number of sequences that may be amplified, or, stated another way, the number of amplicons that may be generated, by a multiplex amplification is dictated in large part by the number of different amplification primer pairs used during the multiplex amplification. According to certain embodiments of the invention, each amplification primer pair includes two amplification primers, one forward amplification primer and one reverse amplification primer, as is well-known in the art. The amplification primer pairs may be sequence-specific and may be designed to hybridize to sequences that flank a sequence of interest to be amplified. Thus, the actual nucleotide sequences of each primer pair may depend upon the sequence of interest to be amplified, and will be apparent to those of skill in the art. Methods for designing primer pairs suitable for amplifying specific sequences of interest via PCR or RT-PCR are well-known. See e.g., Eckert et al. (1991) PCR: A Practical Approach, McPherson, Quirke, and Taylor eds., IRL Press, Oxford, Vol. 1, pp. 225-244; TAQMAN® Universal PCR Master Mix Protocol (available from Applied Biosystems, an Applera Corporation business, Cat. #4304449 Rev. C); Rozen et al., 2000, *Bioinformatics Methods and Protocols: Methods in Molecular Biology*, Humana Press, Totowa, N.J., pp 365-386; which provide examples demonstrating how particular primer pairs may be designed.

Generally, each amplification primer must be sufficiently long to prime the template-directed synthesis of the target sequence under the conditions of the amplification reaction. The exact lengths of the primers may depend on many factors, including but not limited to, the desired hybridization temperature between the primers and template polynucleotides and the complexity of the different target polynucleotide sequences to be amplified. The ability to select lengths and sequences of primers suitable for particular applications is within the capabilities of ordinarily skilled artisans. In certain embodiments, the primers may contain from about 15 to about 35 nucleotides, although the primers may contain more or fewer nucleotides. Short primer molecules generally require lower temperatures to form sufficiently stable hybrid complexes with the template. Generally, the amplification primers should be designed to have a melting temperature ($T_m$) in the range of about 55-75° C. Melting temperatures in this range will tend to insure that the primers remain annealed or hybridized to the target polynucleotide at the initiation of primer extension. The actual temperature used for the primer extension reaction may depend upon, among other factors, the concentration of the primers which are used in the multiplex assays. For amplifications carried out with a thermostable polymerase such as Taq DNA polymerase, the amplification primers can be designed to have a $T_m$ in the range of about 60 to about 78° C. The melting temperatures of the different amplification primers can be different; however, preferably they should all be approximately the same.

$T_m$ can be determined empirically using several standard procedures, based on ultraviolet hypochromism, for example, by monitoring the spectrum at 260 nm (e.g. as described in Biochemistry—The Molecular Basis of Cell Structure and Function, 2nd Edition, Lehninger, Worth Publishers, Inc., 1970, pp. 876-7). The various methods of determining $T_m$ values may produce slightly differing values for the same DNA molecule, but those values typically do not vary from each other by more than about 2° C. or 3° C.

In other embodiments, the $T_m$ values can be calculated using known methods for predicting oligonucleotide melting temperatures (see, e.g., SantaLucia, 1998, Proc. Natl. Acad. Sci. USA 95:1460-1465; Frier et al., 1986, Proc. Natl. Acad. Sci. USA 83:9373-9377; Breslauer, 1986, Proc. Natl. Acad, Sci. USA 83:3746-3750; Rychlik et al., 1989, Nucleic Acids Res. 17:8543-8551; Rychlik et al., 1989, Nucleic Acids Res. 18:6409-6412; Wetmur, 1991, Crit. Rev. Biochem. Mol. Biol. 26:227-259; Osborne, 1991, CABIOS 8:83; Montpetit et al., 1992, J. Virol. Methods 36:119-128).

Like amplification primers for conventional PCR or RT-PCR, the sequences of amplification primer pairs useful for multiplex amplifications are designed to be substantially complementary to regions of the target polynucleotides that flank the sequence of interest to be amplified. By "substantially complementary" is meant that the sequences of the primers include enough complementarity to hybridize to the target polynucleotides under the temperature and conditions employed in the multiplex amplification reaction.

Although in many instances the sequences of the primers may be completely complementary to the template polynucleotide, in some instances it may be desirable to include regions of mis-match or non-complementarity, as is well known in the art. As a specific example, a region of non-complementarity may be included at the 5'-end of one or more of the primers, with the remainder of the primer sequences being completely complementary to their respective target polynucleotide sequences. As another specific example, non-complementary bases or longer regions of non-complementarity can be interspersed throughout the primer, provided that the primer has sufficient complementarity to hybridize to the target polynucleotide sequence under the temperatures and reaction conditions used for the multiplex amplification.

One or more of the primers can include a label, e.g., at the 5' terminus. The term "label" refers to any moiety that, when attached to compounds such as polynucleotides, render such compounds detectable using known detection means, e.g., spectroscopic, photochemical, radioactive, biochemical, immunochemical, enzymatic or chemical means. Exemplary labels include but are not limited to fluorophores, chromophores, radioisotopes, spin labels, enzyme labels, infrared labels, and chemiluminescent labels. Other examples of labels include members of conventional binding pairs, such as biotin, which may be used with avidin in a capture method or for further concentrating the sample. Patents teaching the use of such labels include U.S. Pat. Nos. 3,817,837; 3,850,752; 3,939,350; 3,996,345; 4,277,437; 4,275,149; and 4,366,241. Means of detecting such labels are well known to those of skill in the art.

In certain embodiments, primers can also include a 5'"tail" (see, e.g., Bengra et al., 2002, Clin. Chem. 48:2131-2140 and Myakishev et al., 2001, Genome Res. 11:163-169) for universal amplification, detection and/or purification. In some embodiments, primers can include a tag portion for binding to a tag-complement portion of a mobility modifier (see, e.g., U.S. Pat. No. 6,395,486 to Grossman). Exemplary tags and/or tag complements include but are not limited to antibodies and associate antigen or hapten, receptors and associated ligands, avidin (or streptavidin) and biotin, and polynucleotide sequences and their complementary sequences. A mobility modifier typically also includes a tail portion, such as a polymer, for effecting a particular mobility a mobility-dependent analysis technique.

The chemical composition of the amplification primers is not critical to the success of the multiplex amplifications described herein. The only requirement is that the DNA polymerase used in the multiplex amplification reaction be able to extend the primers when hybridized to a target polynucleotide. A variety of oligonucleotides that are capable of being extended by DNA polymerases in template-dependent primer extension reactions are known in the art. Examples of these oligonucleotides include, but are not limited to, DNA, RNA, PNA and LNA oligonucleotides, or various combinations and/or chimeras thereof. For example, a chimeric oligonucleotide can comprise a region of DNA fused to a region of, for example, RNA, PNA or LNA. As a specific example, a chimeric amplification primer may include two regions of PNA linked by a 2'-deoxyribonucleotide or region of DNA (see, e.g., International publication No. WO/9640709, incorporated herein by reference, for methods and compositions related to PNA/DNA chimera preparation). The amplification primers may be wholly composed of the standard gene-encoding nucleobases (e.g., cytidine, adenine, guanine, thymine and uracil) or, alternatively, they may include modified nucleobases known by skilled artisans to form base-pairs with the standard nucleobases and to be extendible by polymerases when included in primers. Specific examples of such modified nucleobases include, but are not limited to, 7-deazaguanine and 7-deazaadenine. Other suitable modified or nonstandard nucleobases will be apparent to those of skill in the art.

In addition, the amplification primers may include one or more modified interlinkages, such as one or more phosphorothioate or phosphorodithioate interlinkages, as is well-known in the art.

All of these types of various oligonucleotides, or mixtures of such oligonucleotides, may be used as amplification primers in the various multiplex amplifications described herein. In one embodiment, all of the primers used in the multiplex amplification reaction are DNA oligonucleotides.

The number of different amplification primer pairs utilized in the multiplex amplification is not critical and can range from as few as two, to as many as tens, hundreds, thousands, or even more. Thus, depending upon the particular application and conditions, the multiplex amplifications permit the simultaneous amplification of from as few as two, to as many as tens, hundreds, thousands, or even more, polynucleotide sequences of interest.

As will be described in more detail below, the product of a multiplex amplification can be used in a variety of different downstream assays and/or analyses. In a specific embodiment that will be discussed further, below, the product of a multiplex amplification reaction may be used in a plurality of subsequent, single-plex ("simplex"), quantitative or real-time PCR amplification reactions, such as for example, the quantitative or real-time amplifications routinely employed for gene expression analysis and which are commonly known in the art as 5'-exonuclease assays or TAQMAN® assays (see, e.g., U.S. Pat. No. 5,691,146). When the product of the multiplex amplification reaction is to be used in this manner, the number of and/or sequences of the amplification primer pairs utilized in the multiplex amplification reaction can be correlated to correspond to the number of downstream single-plex, quantitative amplification reactions that may be performed. For example, if 96 downstream single-plex 5'-exonuclease amplification assays are desired, then the multiplex amplification can be carried out with a pool of 96 different sets of amplification primers or pairs. Correlating the number of amplification primer pairs with the number of subsequent single-plex quantitative amplification reactions is particularly convenient or advantageous in embodiments in which each subsequent single-plex quantitative amplification reaction will be carried out with a pair of amplification primers identical in sequence to one of the pairs used in the multiplex amplification reaction.

The number and/or sequences of the amplification primer pairs used for a multiplex amplification reaction can be correlated in a similar manner to other downstream assays or analyses that may be performed with the product of the multiplex amplification reaction. For example, in embodiments where the product of the multiplex amplification reaction will be used for gene expression analysis on, for example, an oligonucleotide array, the multiplex amplification primer pairs can be designed to specifically amplify the polynucleotide sequences that will be assessed by the microarray.

The sequences of multiplex primer pairs suitable for generating multiplex amplification product suitable for use in particular desired subsequent analyses and/or assays will be apparent to those of skill in the art.

As discussed above, depending upon the nature of the sample polynucleotides to be amplified (e.g., RNA or DNA), a multiplex amplification reaction can be accomplished by polymerase chain reaction (PCR) or reverse-transcription PCR (RT-PCR). Thus, multiplex amplifications in which the target polynucleotide(s) is a DNA will typically include as essential components, in addition to the plurality of amplification primer pairs or sets discussed above, a mixture of 2'-deoxribonucleoside triphosphates suitable for template-dependent DNA synthesis (e.g., primer extension) and a DNA polymerase. Multiplex amplifications in which the target polynucleotide(s) is a RNA will typically additionally include a reverse-transcriptase. With the exception of certain parameters described below, and the use of a plurality of amplification primer pairs instead of a single pair as described above, the multiplex amplification reactions may be carried out using reagents, reagent concentrations and reaction conditions conventionally employed in such conventional PCR and RT-PCR reactions. For example, except as noted herein, the various different primer concentrations, enzymes (e.g.

DNA polymerases and reverse transcriptases), enzyme concentrations, dNTP mixtures (as well as their absolute and/or relative concentrations), total target polynucleotide concentrations, buffers, buffer concentrations, pH ranges, cycling times and cycling temperatures employed in conventional PCR and RT-PCR reactions may be used for the multiplex amplification reactions described herein. Guidance for selecting suitable reaction conditions may be found, for example, in U.S. Pat. Nos. 4,683,202; 4,683,195; 4,800,159; 4,965,188; 5,561,058; 5,618,703; 5,693,517, 5,876,978; 6,087,098; 6,436,677; and 6,485,917, and PCR Essential Data, J. W. Wiley & Sons, Ed. C. R. Newton, 1995, and PCR Protocols: A Guide to Methods and Applications. (Innis, M, Gelfand, D., Sninsky, J. and White, T., eds.), Academic Press, San Diego (1990), all of which are incorporated herein by reference. A variety of tools for designing PCR and RT-PCR amplification primers, as well as myriad protocols, reaction conditions and techniques for carrying out various different types of PCR reactions, including conventional PCR reactions and RT-PCR reactions are also available online. All of these various tools and protocols can be used in connection with the multiplex amplification reactions described herein.

Like conventional PCR and RT-PCR amplification reactions, the multiplex amplification reactions may be carried out with a variety of different DNA polymerases (or mixture of DNA polymerases), but are preferably carried out in the presence of one or more thermostable polymerases. Suitable thermostable polymerases include, but are not limited to, Taq and Tth (commercially available from Applied Biosystems, an Applera Corporation business). Moreover, like conventional RT-PCR amplification reactions, multiplex RT-PCR amplification reactions may be carried out with a variety of different reverse transcriptases (or mixture of reverse transcriptases), although in some embodiments thermostable reverse-transcriptions are preferred. Suitable thermostable reverse transcriptases include, but are not limited to, reverse transcriptases such as AMV reverse transcriptase, MuLV, and Tth reverse transcriptase. Temperatures suitable for carrying out the various denaturation, annealing and primer extension reactions with the polymerases and reverse transcriptases are well-known in the art. Optional reagents commonly employed in conventional PCR and RT-PCR amplification reactions, such as reagents designed to enhance PCR, modify $T_m$, or reduce primer-dimer formation, may also be employed in the multiplex amplification reactions (see e.g., U.S. Pat. Nos. 6,410,231; 6,482,588; 6,485,903; and 6,485,944, all of which are incorporated herein by reference). In certain embodiments, the multiplex amplifications may be carried out with commercially-available amplification reagents, such as, for example, AMPLITAQ® Gold PCR Master Mix, TAQ-MAN® Universal Master Mix and TAQMAN® Universal Master Mix No AMPERASE® UNG, all of which are available commercially from Applied Biosystems, an Applera Corporation business.

Although suitable results can be achieved using conventional reagents and reaction conditions, in many embodiments the performance or observed efficiency of a multiplex amplification can be improved by adjusting certain parameters and/or conditions of the reaction.

The expressions "observed performance" and "observed efficiency" and grammatical equivalents thereof when used in connection with multiplex amplifications refer to the amounts of the individual amplicons generated in the multiplex amplification. Amplification performance or efficiency can correspond to a multiplex amplification generally, or to a specific amplicon within a multiplex amplification. A multiplex amplification is 100% efficient for a specific amplicon of interest when the quantity of the specified amplicon generated in the multiplex amplification is identical to that produced in a single-plex, conventional PCR or RT-PCR reaction with the same target polynucleotide. A multiplex reaction is 100% efficient generally when the amounts of each of the amplicons produced in the multiplex amplification are identical to the amounts of the respective amplicons produced in individual, single-plex conventional PCR or RT-PCR reactions with the same target polynucleotides. Multiplex amplifications are considered "highly efficient" for a specific amplicon when the amount of the specified amplicon generated in a multiplex reaction is within about $\geq 90\%$ of the amount generated in a single-plex, conventional PCR or RT-PCR reaction.

The observed efficiency of a multiplex amplification reaction, either generally or with respect to a specified target sequence, can be assessed using real-time PCR methods. In one embodiment, the observed efficiency of amplification of a specific target sequence can be determined by amplifying a plurality of polynucleotides, which includes the specific target, in a multiplex PCR amplification reaction using a plurality of primer sets, each of which is suitable for amplifying a different target sequence of interest. The multiplex amplification is carried out for N thermal cycle steps, where N can be selected by the user. A first aliquot of multiplex amplification product is then amplified in a single-plex PCR amplification reaction in the presence of an amplification primer pair or set suitable for amplifying the target sequence of interest and a reagent useful for monitoring the amplification reaction in real time, such as an intercalating dye or a sequence-specific oligonucleotide probe (e.g., a TaqMan probe). A second aliquot obtained from a "mock" (control) multiplex amplification that was not subjected to thermal cycling is similarly single-plex amplified. A $Ct^{assay}$ value is obtained from the first aliquot and a $Ct^{control}$ value is obtained from the second aliquot. In one embodiment, the observed efficiency of the amplification of the specified target sequence in the multiplex amplification can be calculated from the following equation:

$$\% \text{ observed efficiency} = 100 \times (Ct^{control}\text{value} - Ct^{assay}\text{value})/N$$

Any number of specific target sequences in a multiplex amplification can be similarly analyzed. A user can select a selection criteria (i.e. a "cut-off" value) for the observed efficiency such as, for example, 50%, 70%, 80%, 90%, 95% or 99%. If desired, the observed efficiencies for each primer set in a multiplex amplification can be determined and the primers grouped according to whether their observed efficiencies equal or exceed the selection criteria. Primer sets that do not meet or exceed the selection criteria can be analyzed individually in singleplex amplifications, or can be re-grouped into one or more separate pools of primer sets for further analysis.

In another embodiment, the average observed efficiency of amplification of all of the target sequences in a multiplex amplification can be analyzed. As for the embodiment discussed above, a multiplex amplification can be carried out for N thermal cycles, the exact number of which can be selected by the user. The product of the multiplex amplification is divided into a plurality of aliquots, typically into a number of aliquots equal to the number of primer pairs used in the multiplex amplification. Each aliquot is single-plex amplified in the presence of one of the sets of primer pair used in the multiplex amplification and a reagent or probe suitable for each single-plex amplification and an average $Ct^{assay}$ value calculated therefrom. $Ct^{control}$ values and an average $Ct^{control}$ value are similarly obtained from single-plex amplifications of a "mock" (control) multiplex amplification reaction that was not subjected to thermal cycling. In one embodiment, the average efficiency of the multiplex amplification can be calculated using the following equation:

$$\% \text{ average efficiency} = 100 \times (\text{average } Ct^{control}\text{value} - \text{average } Ct^{assay}\text{value})/N$$

As will be recognized by skilled artisans, a particular degree of efficiency for a multiplex amplification generally, or for a specific sequence or sequences, is not required for success. All that is required is that the multiplex amplification perform in a manner suitable for a particular application. As discussed above, in many embodiments suitably efficient multiplex amplifications are achieved using conventional PCR or RT-PCR reaction conditions. However, it has been discovered that the efficiency of multiplex amplifications can be improved beyond that achieved using conventional PCR or RT-PCR reaction conditions by modifying certain of the reaction conditions or parameters, such as the quantity of DNA polymerase used.

Typically, conventional PCR and RT-PCR reactions are carried out with 0.05 U/µL DNA polymerase. For a 10 cycle 95-plex amplification carried out with 1 U/20 µL AMPLITAQ GOLD® DNA polymerase (Applied Biosystems, an Applera Corporation business), it has been found that adding an additional 1-8 U/20 µL increases the efficiency of the multiplex amplification. As will be described in more detail in the Examples section, significant increases in efficiency were observed with an additional 1-5 U/20 µL AMPLITAQ GOLD® DNA polymerase. Increases were also observed with an additional 6-15 U/20 µL, but they were less pronounced, potentially, due to the additional glycerol added to the reaction mixture as a result of spiking the reaction mixture with AMPLITAQ GOLD® DNA polymerase stored in 50% glycerol. (see, e.g., FIG. 3). Similar increases in efficiency are also expected for other DNA polymerases, such as, for example. TaqI polymerase, Klenow fragment of DNA polymerase I, SEQUENASE 1.0 and SEQUENASE 2.0 (U.S. Biochemical), T5 DNA polymerase and Phi29 DNA polymerase. Thus, in one embodiment, a multiplex amplification is carried out in the presence of from about 2, 3, 4, 5, 6, 7, 8, 9, 10, 11, 12, 13, 14, 15 or 16 Units DNA polymerase per every 20 µL of reaction volume.

The efficiency of a multiplex amplification reaction may also be increased by employing a longer duration for the primer extension reaction than is typically used in conventional PCR or RT-PCR, either alone or in combination with the increased amount of DNA polymerase discussed above. In conventional PCR and RT-PCR reactions, the primer extension reaction is typically carried out for approximately 1 min. per amplification cycle. While not intending to be bound by any particular theory of operation, it is believed that increasing the duration of the primer extension reaction from 1 min. to, for example, about 2, 3, 4, 5, 6, 7, 8, 9, 10 min. or even longer, may improve the performance or efficiency of a multiplex amplification. Thus, in one embodiment, a multiplex amplification is carried out using a duration for the primer extension reaction in the range of about 2-15 min. per cycle. The durations used for the other intervals making up a single reaction cycle can be those used conventionally. In one embodiment, a multiplex amplification may be carried out using a two-step cycle including a first denaturation step of 95° C. for 15 seconds and a second anneal/extend step of 60° C. for 1 to 15 minutes.

Conventional PCR and RT-PCR employ concentrations of amplification primers in the range of about 300-900 nM each primer. Although primer concentrations in this range can be used in the multiplex amplifications, it has been discovered that multiplex amplifications may be carried out using considerably lower amplification primer concentrations. Quite surprisingly, in 95-plex amplifications carried out for 10 cycles using a primer extension reaction time of 10 min/cycle, highly efficient multiplex amplification was achieved with primer concentrations as low as 45 nM each primer. In certain embodiments, primer concentrations in the range of about 30-45 nM each primer may be used.

Moreover, it was discovered that it is not necessary to optimize the concentrations of the individual primer pairs. Regardless of the sequences being amplified, and hence the sequences of the primers, the amplification primers can be used at concentrations in the range of about 30-900 nM each primer. Different amplification primer pairs may be present at different concentrations within this range or, alternatively, some or all of the amplification primers may be present at approximately equimolar concentrations within this range. In one embodiment, at least some of the amplification primers, for example, approx. 10%, 25%, 35%, 50%, 60%, or more, are present in approximately equimolar concentrations ranging from about 30 nM to about 100 nM each primer. In another embodiment, all of the amplification primers are present at approximately equimolar concentrations in the range of about 30 nM to 100 nM each primer. In certain embodiments, all of the amplification primers are present at concentrations of 30, 40, 45, 50, 60, 70, 80, 90, 100, 200, 300, 400, 500, 600, 700, 800 or 900 nM each primer. In yet another embodiment, some or all of the amplification primers are present in a concentration of about 45 nM each primer. The amplification primer concentrations discussed above can be used regardless of whether the target polynucleotide(s) being multiplex amplified are RNA or DNA. The reverse-transcription reaction of a multiplex RT-PCR amplification works well at the stated primer concentrations.

As will be recognized by skilled artisans, PCR and RT-PCR reactions can be broken up into three phases: an exponential phase in which the amount of amplicon accumulates exponentially every cycle (i.e., doubles every cycle); a linear phase in which the amount of amplicon accumulates at a variable rate every cycle (i.e., the reaction begins to slow); and a plateau phase, where the reaction has stopped, no more amplicon is being produced and, if left long enough, the amplicon will begin to degrade.

In the exponential phase, the degree of amplification achieved is exponentially proportional to the number of amplification cycles employed. For example, a 10-cycle amplification yields a 1024-fold increase in the quantity of amplified sequence. As another example, a 15-cycle amplification yields a 32,286-fold increase. In another example, a 20-cycle amplification yields a 1,048,576-fold increase.

The number of amplification cycles performed with a multiplex amplification may depend upon, among other factors, the degree of amplification desired. The degree of amplification desired, in turn, may depend upon such factors as the amount of polynucleotide sample to be amplified and/or the intended downstream use of the multiplex amplification product. Accordingly, the number of cycles employed in a multiplex amplification will vary for different applications and will be apparent to those of skill in the art. For most applications, reactions carried out for 10 amplification cycles are expected to yield sufficient multiplex amplification product for several hundred downstream analyses, even when the sample is derived from 1 to a few cells, is present in very low copy number, and/or is present only as a single copy, regardless of the amount of sample required to perform the analysis. However, more or fewer amplification cycles may be employed. In certain embodiments the multiplex amplification is carried out for as many as 10, 11, 12, 13, 14, 15, 16, 17, 18, 19, 20, or more cycles. In specific embodiments, the multiplex amplification is carried out for 2-12 cycles, inclusive, for 5-11 cycles, inclusive, or for up to 14 cycles (e.g., see Example 7). A high number of cycles may be required in certain applications where a large plurality of downstream assays are to be performed.

In many embodiments, it may be desirable to keep the multiplex amplification from progressing beyond the exponential phase or the linear phase. Indeed, in many embodiments, it may be desirable to carry out the multiplex amplification for a number of cycles suitable to keep the reaction within the exponential or linear phase.

Multiplex amplification reaction parameters (e.g., concentrations of primer pairs or sets, concentration of DNA polymerase, duration and annealing, primer extension and/or denaturation steps, number of thermal cycles, $Mg^{2+}$ concentration, concentration of adjuvants (such as DMSO, glycerol, BSA or urea) can be optimized empirically, for example by carrying out a plurality of multiplex amplifications varying one (or more) of these parameters and assessing the efficiencies of the resultant multiplex amplifications, for example using the methods described above. An example of such an optimization reaction, in which the amount of DNA polymerase was varied, is described in Example 1, below.

Once amplified, the multiplex amplification product can be used in myriad different subsequent assays or analyses without further purification or manipulation. For such subsequent assays or analyses, the product of the multiplex amplification can be divided, either with or without prior dilution, amongst a plurality of different assays or analyses. The degree of any optional dilution may depend upon such factors as the number of subsequent analyses desired and the amount of sample required for each such analysis, and will be apparent to those of skill in the art. Examples of subsequent assays and analyses that can be carried out with a multiplex amplification product, but are not limited to, single nucleotide polymorphism (SNP) analysis, genotyping analysis, gene expression analysis (e.g., via quantitative PCR or RT-PCR or via hybridization on oligonucleotide microassays), finger printing analysis, nucleic acid sequencing (e.g., U.S. Pat. No. 6,428,986), nucleic acid mini-sequencing (e.g., U.S. Pat. No. 6,479,242), and/or for hybridizing to arrays that may be used in gene expression profiling (e.g., U.S. Pat. No. 6,485,944).

In certain embodiments, the product of the multiplex amplification is not divided amongst a plurality of different assays or analyses. For example, one or more amplification primers, probes, dyes and/or other reagents may be added directly to the amplification product in order to carry out additional amplifications. In various other embodiments, the product of the multiplex amplification is divided amongst a plurality of aliquots, and one or more of these aliquots can be subject to a multiplex assay or analysis, examples of which include multiplex amplification and multiplex SNP detection.

In one specific embodiment, the product of the multiplex amplification may be used in subsequent amplification reactions, such as the quantitative or real-time amplification assays commonly used for gene expression analysis. In a specific example of such a quantitative or real-time amplification assays, total RNA from a sample is amplified by RT-PCR in the presence of amplification primers suitable for specifically amplifying a specified gene sequence of interest and an oligonucleotide probe labeled with a labeling system that permits monitoring, for example via the 5'-exonuclease activity of the DNA polymerase employed in the RT-PCR amplification, of the quantity of amplicon that accumulates in the amplification reaction in real-time. The cycle threshold values (Ct values) obtained in such quantitative RT-PCR amplification reactions can be correlated with the number of gene copies present in the original total mRNA sample. Such quantitative or real-time RT-PCR reactions, as well as different types of reagents and/or labeled oligonucleotide probes useful for monitoring the amplification in real time, are well-known in the art. A specific assay which utilizes the 5'-exonuclease assay to monitor the amplification as a function of time is referred to as the 5'-exonuclease gene quantification assay (see, e.g., U.S. Pat. Nos. 5,210,015 and 5,538,848 and Lie & Petropoulos, 1998, Curr. Opin. Biotechnol. 14:303-308). Another specific assay, which utilizes intercalating or other dyes to monitor an amplification as a function of time, is described in U.S. Pat. No. 5,994,056.

Although powerful, 5'-exonuclease gene quantification assays (as well as other gene quantification assays, such as quantification assays performed on DNA microarrays) require relatively large amounts of starting RNA (e.g., from 1-10 μg). Owing to this large sample requirement, 5'exonuclease gene quantification assays and other gene quantification assays have not been suitable for detecting genes expressed at low copy numbers, or in instances where only limited quantities of sample is available (e.g., from clinical biopsies, etc.).

By virtue of the ability to amplify simultaneously a plurality of polynucleotide sequences in a sample, the multiplex amplification reactions described herein are ideal for use in connection with the such downstream gene expression analyses, such as, for example the 5'-exonuclease gene quantification assay. Polynucleotides present in samples at extremely low copy numbers, and/or samples obtained from a few or even a single cell, may be multiplex amplified so as to provide amounts of sample suitable for tens, hundreds or even thousands of quantitative or real-time amplification assays. Accordingly, in one embodiment of the invention, the product of the multiplex amplification reaction is divided, either with or without prior dilution, amongst a plurality of single-plex quantitative or real-time amplification reactions. Each single-plex quantitative or real-time amplification reaction is carried out in a conventional manner with a single set of amplification primers and a suitable probe. The amplification primer pair or set used for the single-plex quantitative or real-time amplification can be the same as one of the primer pairs or sets used in the multiplex amplification reaction. Significantly, the multiplex amplification product can be used directly in such subsequent single-plex amplifications without further purification or manipulation. The various enzymes, dNTPs, amplification primers and other optional reagents carried over from the multiplex amplification do not interfere with the accuracy of the subsequent quantitative or real-time amplification assays.

The present inventor has surprisingly discovered, in certain embodiments, that the multiplex amplification substantially maintains the copy number ratios, presumably due to high efficiency of amplification, so that the copy numbers or expression levels of the original sample can be ascertained from the multiplex amplified sample. In some embodiments, relative copy numbers from the original sample can thus be determined and used, for example, in various downstream applications, such as gene expression studies.

Samples amplified in a multiplex fashion may be used in a wide variety of subsequent analysis or assay without further purification or manipulation. For example, the product of the multiplex amplification may be used for single polynucleotide polymorphism ("SNP") analysis, genotyping analysis, gene expression analysis, fingerprinting analysis, analysis of gene mutations for genetic diagnoses, analysis of rare expressed genes in cells, nucleic acid sequencing (e.g., U.S. Pat. No. 6,428,986), and nucleic acid mini-sequencing (e.g., U.S. Pat. No. 6,479,242).

In performing gene expression studies, for example, various methods for quantifying a polynucleotide product in the multiplex amplified sample can be used. The term "quantifying" when used in the context of quantifying transcription levels of a gene can refer to absolute or to relative quantification. Absolute quantification may be accomplished by inclusion of known concentration(s) of one or more target nucleic acids (e.g. control nucleic acids or with known amounts the target nucleic acids themselves) and referencing the detected signal of unknowns with the known target nucleic acids (e.g. through generation of a standard curve). Alternatively, relative quantification can be accomplished by comparison of detected signals between two or more genes, or between two or more treatments to quantify the changes in detected signal values and, by implication, transcription level. The detected signal will depend upon the particular method utilized. For example, when using real-time PCR, the detected signal can be related to a fluorescence intensity. Amplification products can be separated and detected by any of a variety of techniques known to those of skill in the art (see, e.g., U.S. Pat. No. 6,618,679). The data obtained from the detection can be stored and analyzed to obtain a set of gene expression data. When using a microfabricated DNA array, the detected signal can be a hybridization intensity.

In particular embodiments, the product of a multiplex amplification can be applied to solid supports containing polynucleotide hybridization probes for differentially expressed genes. Any solid surface to which polynucleotides can be bound, either directly or indirectly, either covalently or non-covalently, can be used. Non-limiting examples of such supports include filters, polyvinyl chloride dishes, beads, glass slides etc. A particular example of a solid support is a high density array or DNA chip. These contain a particular hybridization probe in a predetermined location on the array. In some embodiments, each predetermined location may contain more than one molecule of the probe, but each molecule within the predetermined location has an identical sequence. Such predetermined locations are termed features. There may be, for example, from 2, 10, 100, 1000, to 10,000, 100,000, or 400,000 of such features on a single solid support. The solid support, or the area within which the probes are attached may be on the order of a square centimeter. Hybridization probe arrays for expression monitoring can be made and used according to any techniques known in the art. (See for example, Lockhart, D. J. et al., 1996, Nature Biotechnology 14:1675-1680; McGall, G. et al., 1996, Proc. Nat. Acad. Sci. USA 93:13555-13460; and U.S. Pat. Nos. 6,033,860, 6,309, 822, 6,485,944, and 6,548,257).

The present inventor has surprisingly discovered that the presence of conventional concentrations of oligonucleotide probes, such as 5'-exonuclease probes, in a multiplex amplification reaction does not interfere with the performance or efficiency of the multiplex amplification. Nor does the presence of such probes interfere with downstream analyses, such as single-plex quantitative or real-time amplification assays or other analyses, carried out with the product of the multiplex amplification. This discovery permits multiplex amplifications to be carried out using commercially-available, off-the-shelf quantitative or real-time amplification reagents, such as the Assays-On-Demand reagents commercially available from Applied Biosystems (an Applera Corporation business).

The ability to carry out a multiplex amplification with commercially available Assays-On-Demand 5'-exonuclease reagents (or other commercially-available reagents) permits the creation of multiplex amplification reactions that are ideally correlated or matched with subsequent single-plex 5'-exonuclease assays. By correlated or matched is meant that the same sets of primers or primer pairs that are used in the multiplex amplification step may be used in the downstream analytical assays. However, in some embodiments, the primers or primer pairs used in the downstream assays may be different from the primer pairs used in the upstream multiplex amplification. In certain embodiments, the primers used in a the downstream assays may or may not be nested primers.

Quite advantageously, kits suitable for carrying out a multiplex amplification followed by a plurality of single-plex quantitative or real-time amplification assays can be readily created from readily-available 5'-exonuclease reagents without requiring additional manipulations or purification. The primers for performing the multiplex amplification can be created by pooling together 5'-exonuclease reagents comprising a pair of amplification primers and a 5'-exonuclease probe. As mentioned above, the presence of the 5'-exonuclease probes in the multiplex amplification reaction and subsequent single-plex 5'-exonuclease amplification assays does not interfere with either amplification.

An embodiment of a matched or correlated multi-step assay, which can be created using the ASSAYS-ON-DEMAND® service available from Applied Biosystems, available at the on-line website product's section, is illustrated there, where a plurality of 5'-exonuclease amplification primer/probe sets are selected by the user and pooled together to yield a plurality of amplification primer pairs or sets suitable for multiplex amplification (the pool also includes the plurality of 5'-exonuclease probes). A separate aliquot of each of the selected 5'-exonuclease amplification primer/probe sets are dispensed into individual reaction vessels, such as the wells of a multiwell plate, a single primer/probe set per vessel or well. In a first step, target polynucleotides from a sample of interest are multiplex amplified in the presence of the pooled amplification 5'-exonuclease primers/probes. The product of the multiplex amplification is then aliquoted into the wells of the multiwell plate, and single-plex 5'-exonuclease amplification assays are carried out using conventional methods. In one particularly convenient embodiment, the 5'-exonuclease primer/probe sets may be dispensed among the wells of a micro fluidic card that can be used directly on an instrument designed for quantitative or real-time amplification analysis, such as the AB Prism 7900 HT instrument available from Applied Biosystems (an Applera Corporation business). An example of a suitable microcard is described in U.S. Pat. No. 6,126,899 and a commercial embodiment is the 7900HT Micro Fluidic card available from Applied Biosystems (an Applera Corporation business).

Oligonucleotide probes that can be present in the multiplex amplification are not limited to 5'-exonuclease probes. In one embodiment, any labeled or unlabeled single-stranded oligonucleotide which is complementary to all or part of an amplified target sequence, may be present in the multiplex amplification.

Like the primers discussed above, such oligonucleotide probes may be DNA, RNA, PNA, LNA or chimeras composed of one or more combinations thereof. The oligonucleotides may be composed of standard or non-standard nucleobases or mixtures thereof and may include one or more modified interlinkages, as previously described in connection with the amplification primers. The oligonucleotide probes may be suitable for a variety of purposes, such as, for example to monitor the amount of an amplicon produced, to detect single nucleotide polymorphisms, or other applications as are well-known in the art.

In one embodiment, each oligonucleotide probe is complementary to at least a region of a specified amplicon. The probes can be completely complementary to the region of the specified amplicons, or they may be substantially complementary thereto (at least about 65% complementary over a stretch of at least 15 to 75 nucleotides). In other embodiments, the probes are at least about 75%, 85%, 90%, or 95% complementary to the regions of the amplicons. See Kanehisa, M., 1984, Nucleic Acids Res. 12: 203, incorporated herein by reference. The exact degree of complementarity between a specified oligonucleotide probe and amplicon will depend upon the desired application for the probe and will be apparent to those of skill in the art.

The lengths of such oligonucleotide probes can vary broadly, and in some embodiments can range from as few as two as many as tens or hundreds of nucleotides, depending upon the particular application for which the probe was designed. In one specific embodiment, the oligonucleotide probes range in length from about 15 to 35 nucleotides. In another specific embodiment, the oligonucleotide probes range in length from about 15 to 25 nucleotides. In yet another specific embodiment, oligonucleotide probes can range from 25 to 75 nucleotides. In other embodiments, the probes range in length from about 6 to 75 nucleotides or from about 12 to 22 nucleotides. An oligonucleotide probe can include a 5' tag portion for binding with a mobility modifier (e.g., as described in U.S. Pat. No. 6,395,486).

In one specific embodiment, oligonucleotide probes present in a multiplex amplification are suitable for monitoring the amount of amplicon(s) produced as a function of time. Such oligonucleotide probes include, but are not limited to, the 5'-exonuclease assay (TAQMAN®) probes described above (see also U.S. Pat. No. 5,538,848), various stem-loop molecular beacons (see, e.g., U.S. Pat. Nos. 6,103,476 and 5,925,517 and Tyagi & Kramer, 1996, Nature Biotechnology 14:303-308), stemless or linear beacons (see, e.g., WO 99/21881), PNA MOLECULAR BEACONS™ (see, e.g., U.S. Pat. Nos. 6,355,421 and 6,593,091), linear PNA beacons (see, e.g. Kubista et al., 2001. SPIE 4264:53-58), non-FRET probes (see, e.g., U.S. Pat. No. 6,150,097), SUNRISE®/AMPLIFLUOR® probes (U.S. Pat. No. 6,548,250), stem-loop and duplex SCORPION™ probes (Solinas et al., 2001, Nucleic Acids res. 29: E96 and U.S. Pat. No. 6,589,743), bulge loop probes (U.S. Pat. No. 6,590,091), pseudo knot probes (U.S. Pat. No. 6,548,250), cyclicons (U.S. Pat. No. 6,383,752), MGB ECLIPSE™ probe (Epoch Biosciences), hairpin probes (U.S. Pat. No. 6,596,490), peptide nucleic acid (PNA) light-up probes, self-assembled nanoparticle probes, and ferrocene-modified probes described, for example, in U.S. Pat. No. 6,485,901; Mhlanga et al., 2001. Methods 25:463-471; Whitcombe et al., 1999, Nat. Biotechnol. 17:804-807; Isacsson et al., 2000, Mol. Cell. Probes. 14:321-328; Svanvik et al., 2000, Anal Biochem. 281:26-35; Wolffs et al., 2001. Biotechniques 766:769-771; Tsourkas et al., 2002, Nucleic Acids Res. 30:4208-4215; Riccelli et al., 2002, Nucleic Acids Res. 30:4088-4093; Zhang et al., 2002. Shanghai. 34:329-332; Maxwell et al., 2002, J. Am. Chem Soc. 124:9606-9612; Broude et al., 2002, Trends Biotechnol. 20:249-56; Huang et al., 2002, Chem. Res. Toxicol. 15:118-126; and Yu et al., 2001, J. Am. Chem. Soc. 14:11155-11161, all of which are incorporated herein by reference.

In another embodiment, the oligonucleotide probes are suitable for detecting single nucleotide polymorphisms, as is well-known in the art. A specific example of such probes includes a set of four oligonucleotide probes which are identical in sequence save for one nucleotide position. Each of the four probes includes a different nucleotide (A, G, C and T/U) at this position. The probes may be labeled with labels capable of producing different, detectable signals that are distinguishable from one another, such as different fluorophores capable of emitting light at different, spectrally-resolvable wavelengths (e.g., 4-differently colored fluorophores). Such labeled probes are known in the art and described, for example, in U.S. Pat. No. 6,140,054 and Saiki et al., 1986, Nature 324:163-166.

Performing multiplex amplification in the presence of these various oligonucleotide probes permits a great deal of flexibility in designing or creating sets of amplification primers for multiplex amplifications. Commercially available primer sets including such oligonucleotide probes can be simply pooled together without prior removal of the oligonucleotide probes and used for multiplex amplification without further manipulation.

In some embodiments, the oligonucleotide probes can be removed from pooled primer sets prior to multiplex amplification. Such removal can be effected using pairs of specific binding molecules, such as biotin/avidin or antibody/antigen. For example, a biotin-labeled oligonucleotide probe can be removed by avidin binding. In other embodiments, labeled nucleotide probes can be photobleached using laser or other light sources.

The multiplex amplification may also be carried out in the presence of dye molecules suitable for, for example, monitoring the accumulation of amplification products at the end of the amplification and/or during the amplification as a function of time. In one embodiment, such dyes include dyes that produce a detectable signal, such as a fluorescence, when bound to double-stranded polynucleotides. Non-limiting examples of suitable dyes include common nucleic acid stains, such as intercalating dyes and minor groove binding dyes, as are well-known in the art. In a specific embodiment, the dye is SYBR® Green I or II, ethidium bromide, or YO-PRO-1 (available from Molecular Probes, Eugene, Oreg.). Such dyes can be used at conventional concentrations commonly employed in the art (see, e.g., U.S. Pat. No. 5,994,056).

In carrying out a multiplex amplification in the presence of such a dye molecule, or in the presence of suitable oligonucleotide probes, Applicants have discovered a general method for characterizing pooled sets of primers. In the method, the amplification is monitored in real time, and a cycle threshold value ("$Ct^{pool}$") obtained. This is an additive signal produced by the summation of all of the amplicons. In the embodiment in which oligonucleotide probes are used for the real time multiplex amplification, a separate probe is present for each target sequence being amplified, and all of the probes use the same signaling system. The method is especially useful in providing a rapid and convenient test of pooled reagents that may be provided in ready-made, pre-optimized, kits. Such a pool of reagents can be prepared by mixing commercially available primer sets such as the ASSAYS-ON-DEMAND® Gene Expression products or the primer sets available in the QuantiTect Gene Expression Assays (Qiagen), as further described herein.

In certain applications of the methods described herein, the relative levels of the various polynucleotides in a sample can be determined and compared to a reference sequence (i.e., normalized). The term "reference sequence" refers to a nucleic acid sequence serving as a target of amplification in a sample that provides a control for the assay. The reference may be internal (or endogenous) to the sample source, or it may be an externally added (or exogenous) to the sample. A reference sequence is typically amplified during the multiplex amplification. For example, when performing gene expression analysis, at least one amplification target in a multiplex set that is endogenous to the sample can be selected as a reference sequence. This reference can be a target that has been independently shown to exhibit a fairly constant expression level (for example, a "housekeeping" gene). Examples of such housekeeping genes include GAPDH, β-actin, 18SRNA and cyclophilin. As indicated below, the Ct value from an endogenous reference sequence can provide a control for converting Ct values of other target sequences into relative expression levels. Optionally, a plurality of control targets/reference sequences that have relatively constant expression levels may be included in the multiplexed amplification to serve as controls for each other. Alternatively, the reference sequence can be an external reference sequence. For example, an external reference sequence may be a defined quantity of either RNA, added to the sample prior to reverse transcription, or DNA (e.g., cDNA), added prior to the multiplex amplification.

In an example of the use of a reference sequence, a multiplex polymerase chain reaction amplification is carried out to amplify a sample, such as an RNA or a cDNA sample, using a plurality of primer sets for amplifying target sequences, and including a primer set for amplifying a reference sequence. In real-time single-plex amplifications, a $Ct^{target}$ value is obtained for each target sequence and a $Ct^{ref}$ value is obtained for the reference sequence. In order to normalize the $Ct^{target}$ values, the $Ct^{ref}$ value is subtracted from each $C^{target}$ value to yield a $\Delta Ct^{target}$ value for each target sequence. In certain embodiments, the $Ct^{pool}$ value (as described above) can be used as the reference value. For example, the $Ct^{pool}$ value can be obtained and subtracted from each $Ct^{target}$ value (i.e., the $Ct^{pool}$ value is used in place of the $Ct^{ref}$ value) to yield a $\Delta Ct^{target}$ value.

Certain applications of the present methods concern analyzing samples obtained from a cell, cell line, tissue or organism that has undergone a treatment. For example, up-regulation or down-regulation of certain genes can be analyzed. The term "treatment" refers to the process of subjecting one or more cells, cell lines, tissues, or organisms to a condition, substance, or agent (or combination thereof) that may cause the cell, cell line, tissue or organism to alter its gene expression profile. A treatment may include a range of chemical concentrations and exposure times, and replicate samples may be generated. The term "untreated control" refers to a sample obtained from a cell, cell line, tissue or organism that has not been exposed to a treatment. mRNA (or cDNA) from an untreated control can be amplified in a multiplex amplification in the same manner as a sample from a treated cell, cell line, tissue or organism. Cycle threshold values obtained from both a treated sample and from an untreated control can be normalized, as described above. For example, a cycle threshold value for the untreated control ("$Ct^{untreated}$") can be obtained for each target sequence in the untreated control sample and a $Ct^{ref}$ obtained for each reference sequence, as described above. The $Ct^{ref}$ is subtracted from each $Ct^{untreated}$ value to obtain $\Delta Ct^{untreated}$ values. Similarly, a cycle threshold value ($Ct^{treated}$) for the mRNA (or cDNA) from a sample from a treated cell, cell line, tissue or organism can be obtained and normalized to obtain $\Delta Ct^{treated}$ values. It can be shown that the amount of target sequence from a treated sample normalized to an endogenous reference and relative to a normalized untreated control is given by:

$$2^{-\Delta\Delta Ct}$$

wherein $\Delta\Delta Ct = \Delta Ct^{treated} - \Delta Ct^{untreated}$. The $\Delta\Delta Ct$ values can be used in the analysis of the effect of a treatment on the expressed levels of target sequences.

In practice, in carrying out any of the multiplex or single-plex amplifications described herein, a passive reference containing a fluorescent dye (e.g. ROX) can be included, if desired, to normalize for non-PCR related fluctuations in the fluorescent signal.

Also disclosed herein is a method for characterizing a plurality of amplification primer sets that are suitable for amplifying a plurality of different target sequences of interest. In one embodiment, primer sets are pooled, and used in a multiplex amplification in the presence of a reagent suitable for monitoring the amplification as a function of time. Examples of such a reagent include oligonucleotide probes. Other examples include dye molecules (e.g. intercalating dyes and minor groove binding dyes).

Also provided herein are reagents and kits suitable for carrying out the multiplex amplification and various two-step reactions and/or assays described herein. Such reagents and kits may be modeled after reagents and kits suitable for carrying out conventional PCR and RT-PCR amplification reactions, with the exception that instead of a single set of amplification primers, the reagents and/or kits include a plurality of amplification primers packaged in a single container, wherein the single container may additionally contain one or more oligonucleotide probes, as described herein. Examples of specific reagents include, but are not limited, to the reagents present in ASSAYS-BY-DESIGN™, Pre-Developed Assay Reagents (PDAR) for gene expression. PDAR for allelic discrimination and ASSAYS-ON-DEMAND®, which are commercially available at Applied Biosystems (an Applera Corporation business). The kits may optionally include reagents packaged for downstream or subsequent analysis of the multiplex amplification product. In one embodiment, the kit includes a container comprising a plurality of amplification primer pairs or sets, each of which is suitable for amplifying a different sequence of interest, and a plurality of reaction vessels, each of which includes a single set of amplification primers suitable for amplifying a sequence of interest. The primers included in the individual reaction vessels can, independently of one another, be the same or different as a set of primers comprising the plurality of multiplex amplification primers. In a specific embodiment, both the container and plurality of reaction vessels further include 5'-exonuclease probes such that the kit is suitable for carrying out the multi-step assay illustrated in FIG. 2. In one embodiment, the plurality of reaction vessels is a multiwell plate.

The invention having been described, various features and advantages of the invention are illustrated in the following examples, which are intended to be illustrative and non-limiting.

7. EXAMPLES

7.1 Example 1

Multiplex Amplification Performance Increases with Increasing Concentration of DNA Polymerase To determine the optimal amount of DNA polymerase for performing multiplex amplifications, 95-plex amplifications were carried out as a function of DNA polymerase concentration. The amplification primer mix for the 95-plex amplification was prepared by pooling 10 μL from each of 95 different randomly selected 20× ASSAYS-ON-DEMAND™ Gene Expression Products (Applied Biosystems, an Applera Corporation business, Catalog Nos. Hs0170531_m1; Hs00176369_m1; Hs00176332_m1; Hs00170586_m1; Hs00173565_m1; Hs00176247_m1; Hs00170192_m1; Hs00177127_m1; Hs00176908_m1; Hs00170380_m1; Hs00173925_m1; Hs00170681_m1; Hs00176394_m1; Hs00170633_m1; Hs00173872_m1; Hs00174690_m1; Hs00170288_m1; Hs00173798_m1; Hs00170423_m1; Hs00174927_m1; Hs00174805_m1; Hs00175976_m1; Hs00176222_m1; Hs00173678_m1; Hs00170261_m1; Hs00173592_m1; Hs00174781_m1; Hs00177401_m1; Hs00173854_m1; Hs00173936_m1; Hs00170248_m1; Hs00173564_m1; Hs00174717_m1; Hs00170407_m1; Hs00174575_m1; Hs00174796_m1; Hs00176315_m1; Hs00170969_m1; Hs00153126_o1; Hs00174765_m1; Hs00153510_m1; Hs00173606_m1; Hs00176075_m1; Hs00170236_m1; Hs00170712_m1; Hs00176239_m1; Hs00176121_m1; Hs00171022_m1; Hs00170174_m1; Hs00173506_m1; Hs00174910_m1; Hs0070210_m1; Hs00174789_m1; Hs00174774_m1; Hs00173773_m1; Hs00174937_m1; Hs00173681_m1; Hs00170903_m1; Hs00176268_m1; Hs00176148_m1; Hs00176865_m1; Hs00174599_m1; Hs00170308_m1; Hs00170823_m1; Hs00176077_m1; Hs00173899_m1; Hs00174860_m1; Hs00173717_m1; Hs00175940_m1; Hs00170684_m1; Hs00173526_m1; Hs00170299_m1; Hs00170991_m1; Hs00176385_m1; Hs00175935_m1; Hs00170403_m1; Hs00173855_m1; Hs00170899_m1; Hs00176202_m1; Hs00170349_m1; Hs00177051_m1; Hs00170472_m1; Hs00173634_m1; Hs00175948_m1; Hs00177552_m1; Hs00175997_m1; Hs00174752_m1; Hs00174674_m1; Hs00176505_m1; Hs00176209_m1; Hs00175999_m1; Hs00176998_m1; Hs00176747_m1; Hs00170433_m1; and Hs00174604_ml. Each 20× ASSAYS-ON-DEMAND™ Gene Expression Product contained two unlabeled amplification primers (18 µM each primer) and one FAM-labeled TAQMAN® MGB probe (5 µM). 95-Plex amplifications were carried out with this amplification primer mix using DNA polymerase concentrations ranging from 1 Unit per 20 µL reaction volume (1 U/20 µL) to 17 U/20 µL. For the 95-plex amplification carried out with 1 U/20 µL DNA polymerase, 5 µL pooled primer mix, 10 µL 2× TAQMAN® Universal PCR Master Mix ("2× Master Mix"; Applied Biosystems, an Applera Corporation business, Cat. #4304437) and 5 µL template cDNA (from a cDNA library; 100 ng total cDNA) were added to a reaction tube. 2× Master Mix comprises Gold AMPLITAQ GOLD® DNA polymerase (0.1 U/µL), AmpErase>UNG, dNTPs with dUTP, a passive reference and optimized buffer components. 95-Plex amplifications carried out at higher DNA polymerase concentrations were prepared by spiking the reaction with the appropriate amount of AMPLITAQ GOLD® (5 U/µl; Applied Biosystems Catalog No. N808024). All 95-plex reactions were initially heated (10 min at 95° C.) followed by a total of 10 cycles (15 sec melt at 95° C.; 1 min anneal/extend at 60° C.) on an ABI PRISM® 7700 instrument (Applied Biosystems, an Applera Corporation business).

The product of each 95-plex amplification was diluted to 200 µl with water (10-fold) and divided for 95 individual single-plex real-time amplification reactions. Each single-plex amplification used as primers/probes one of the 20× ASSAYS-ON-DEMAND™ Gene Expression Products described above, with a different set of primers per reaction. The following volumes of reagents were used for the single-plex real-time amplifications: 2 µL diluted 95-plex amplification product, 1 µL 20× ASSAYS-ON-DEMANDT™ Gene Expression Product, 10 µL 2× Master Mix and water to yield a 20 µL reaction volume. All single-plex amplifications were carried out for a total of 40 cycles (using the same cycling conditions as described above) on an ABI PRISM® 7700 or 7900 instrument (Applied Biosystems, an Applera Corporation business). The accumulation of amplicon was monitored in real time. These amplifications are the "assay amplifications."

95 corresponding single-plex control amplifications were carried out in a similar manner with template cDNA that had not been subjected to multiplex preamplification. For each concentration of DNA polymerase, the cycle threshold values (Ct values) of the 95 assay amplifications were obtained and averaged, yielding an average assay Ct value ($Ct^{assay}$) for each DNA polymerase concentration. The Ct values for the 95 control amplifications were also averaged, yielding an average control Ct value ($Ct^{control}$). Differences between the average $Ct^{assay}$ values and average $Ct^{control}$ were obtained (ΔCt values) for each DNA polymerase concentration and plotted (FIG. 3). In this experiment, multiplex amplifications that perform the same as single-plex amplifications (with respect to the amount of amplicon produced) for a particular target sequence yield a ΔCt value of 10. The closer the ΔCt to a value of 10, the better the performance of the 10-cycle multiplex amplification.

As is evident from FIG. 3, the performance of the 95-plex amplification increased with increasing DNA polymerase concentration over a range of 1-5 U/20 µL reaction volume, at which concentration the performance plateaued prior to decreasing slightly. From this experiment, it was determined that the optimal spiked DNA polymerase concentration for carrying out multiplex amplifications using the reaction conditions described above is in the range of 4-6 Units per every 20 µL reaction volume. The decrease in performance observed at higher levels of spiked DNA polymerase is believed to have been caused by exceedingly high concentrations of components of the enzyme storage buffer, e.g. glycerol, in the multiplex amplification reaction.

7.2 Example 2

Multiplex Amplifications are Efficient at Extremely Low Primer Concentrations which do not Require Optimization Two of myriad advantages of multiplex amplifications is the ability to efficiently amplify in a single reaction multiple sequences using extremely low primer concentrations and without having to optimize individually the concentrations of the primers. To demonstrate these points, 100 ng cDNA was multiplex amplified for 0 cycles or 10 cycles in a 95-plex amplification as described in Example 1, using 6 U/20 µL DNA polymerase. Each multiplex amplification was divided and 95 individual single-plex reactions were performed as described in Example 1. The ΔCt value ($Ct^{0\ cycles} - Ct^{10\ cycles}$) for each single-plex reaction was obtained and plotted on a bar graph for visual comparison (FIG. 4). As for Example 1, the optimal ΔCt for a particular reaction is 10. As can be seen from FIG. 4, 90 out of 95 of the assays performed well in the randomly-selected multiplex amplification.

Significantly, none of the primer concentrations were optimized for the 95-plex amplification step. The commercially available 20× Assays-On-Demand reagents were merely pooled together without further manipulation. Moreover, the primer concentrations of the multiplex amplification were extremely low, being present at only 45 nM each primer. In contrast, the primer concentrations used for the single-plex amplifications were 900 nM each primer.

7.3 Example 3

Multiplex Amplifications Can be Carried Out in the Presence of Oligonucleotide Probes Another significant advantage of multiplex amplifications is the ability to carry out the reaction in the presence of oligonucleotide probes without significant interference during either the multiplex amplification or downstream amplifications carried out on the multiplex amplification product. This former advantage is apparent from Example 2, supra. In Example 2, efficient amplification was achieved in the multiplex amplification step, which by virtue of utilizing ASSAYS-ON-DEMAND™ reagents to create the multiplex primer pool, included TAQMAN® MGB oligonucleotide probes in the reaction.

To demonstrate the latter advantage, a single-plex RNase P assay (DNA specific) was run with 1 ng of genomic DNA in the presence or absence of a 5× concentration of the 95-plex primer/probe pool (RNA-cDNA specific) described in Example 1. The 5× concentration of 95-plex primer/probe pool was added to determine what effect it would have on the single-plex RNase assay. The average Ct values of the two reactions are illustrated in FIG. 5. As evident from FIG. 5, the presence of the 95-plex primer/probe pool did not affect the Ct value of the RNase P amplicon, demonstrating that single-plex RNase P assays can be carried out with the product of a multiplex amplification reaction without having to first remove the multiplex primers and/or probes. The presence of the multiplex primers and/or probes does not deleteriously affect the performance of the single-plex RNase P assay.

7.4 Example 4

Multiplex Amplification Permits the Downstream Analysis of very Small Amounts of Sample To demonstrate that multiplex amplifications permit downstream analysis of quantities of sample that would otherwise be too small for the desired type and/or number of analyses, multiplex amplifications were carried out with varying concentrations of sample cDNA ranging from 100 ng to 100 μg (approximately equivalent to a sample size of 5 cells). Each concentration of cDNA was subjected to 95-plex amplification followed by 95 individual real-time amplification analyses as described in Example 1. The average Ct values of the 95-plex amplifications as a function of sample cDNA concentration are provided in FIG. 6. As illustrated in FIG. 6, there is a linear relationship between the sample cDNA concentration and average Ct value, demonstrating that a large percentage (approx. 97%) of the target sequences amplified efficiently, even though they were amplified simultaneously in a multiplexed fashion. The level of sensitivity achieved demonstrates that samples from as few as 1-2 cells can be analyzed by real-time PCR following multiplex amplification. Moreover, the multiplex amplification yields a quantity of amplified sample sufficient for numerous downstream real-time PCR assays.

7.5 Example 5

Multiplex Amplification at Increased Multiplexity

To demonstrate that multiplex amplifications can be carried out at very high levels of complexity, 186-plex, 369-plex, 738-plex and 1013-plex amplifications were carried out in four individual multiplex amplification reactions. The amplification primer mix for each of the amplifications was prepared by pooling equal volumes of 186, 369, 738 or 1013 different randomly selected 20× ASSAYS-ON-DEMAND™ Gene Expression Products into four separate microcentrifuge tubes, respectively. For each of the four tubes, the pooled solution was dried using a SPEEDVAC® concentrator (Thermo Savant, Holbrook, N.Y.). The residue was re-suspended in deionized water such that the multiplexed amplification primers were at a 4× stock concentration (180 nM each primer) relative to the 1× working amplification primer concentration of 45 nM. For the 1013-plex pooled mixture, the combined primers were present in the re-suspension at a concentration of 45.6 μM, and the FAM-labeled TAQMAN® MGB probes were present at 10.1 μM. For the 186-plex amplification, 92 primer sets from each of two plates (designated IAP and IAO) were pooled along with equal volumes of primer sets for two reference genes, glyceraldehyde phosphate dehydrogenase (GAPDH) and cyclophilin. In setting up the experiment described in this Example, for convenience in liquid transfers, each of the above randomly selected 20× ASSAYS-ON-DEMANDT™ Gene Expression Products was distributed into a series of 96-well plates (designated alphabetically plates IAA through IAO). Each 20× Assays-on-Demand Gene Expression Product contained two unlabeled amplification primers (18 μM each primer) and one FAM-labeled TAQMAN® MGB probe (5 μM).

Each of the amplifications (from the 186-, 369-, 738- or 1013-plex pooled primer mixtures) were carried out in a final volume of 50 μL, with the constituents being 12.5 μL of 4× pooled and re-suspended primer mix, 25 μL 2× TAQMAN® Universal PCR Master Mix ("2× Master Mix"; Cat. #4324016 containing no UNG enzyme), 10 μL template cDNA (from a cDNA library; 25 ng total cDNA) and 2.5 μL AMPLITAQ GOLD® DNA polymerase (5 U/μL). The 2× Master Mix included AMPLITAQ GOLD® DNA polymerase (0.1 U/μL), dNTPs, a passive reference and optimized buffer components. Each of the four reactions were carried out for a total of 10 cycles (15 sec. melt at 95° C.; 4 min. anneal/extend at 60° C.) on an ABI PRISM® 7700 instrument.

The product of each amplification was diluted with water and aliquoted for single-plex analysis. In the case of the 186- and 369-plex reactions, the product was diluted 1:5 prior to setting up the single-plex assays. For the 738- and 1013-plex amplifications, the product was diluted 1:10 prior to setting up the single-plex assays. Each of these single-plex amplifications used as primers/probes one of the 20× ASSAYS-ON-DEMAND™ Gene Expression Products used in the multiplex amplification described above and were distributed into a series of 96-well plates for liquid transfer convenience (designated alphabetically plates IAA through IAO). A different set of primer/probes was used in each single-plex reaction. The following volumes of reagents were used for the single-plex ("assay") amplifications: 2.5 μL diluted 186-, 369-, 738- or 1013-plex amplification product, 0.5 μL 20× ASSAYS-ON-DEMAND™ Gene Expression Product, 5 μL 2× Master Mix and water to yield a 10 μL reaction volume. All assay amplifications were carried out for a total of 40 cycles (15 sec. melt at 95° C.; 1 min. anneal/extend at 60° C.) on an ABI PRISM® 7900 instrument. The accumulation of amplicon was monitored in real time.

Corresponding multi-plex control, 186-plex, 369-plex, 738-plex and 1013-plex control amplifications were prepared as described above, but these control multiplex amplifications were not subjected to thermal cycling (i.e., the reactions were not subjected to multiplex amplification). These "mock" amplification mixtures were diluted and assayed in single-plex "control" amplifications as described above. For each assay amplification, the Ct values of the targets from plates IAO and IAP were obtained and averaged, yielding an average assay Ct value. Average ΔCt values were calculated as described in Example 1. The ΔCt values are sorted by ascending ΔCt value in FIG. 7.

The following table summarizes the results from the various assay amplifications:

| Multiplex Reaction | Avg. ΔCt value | Std. Dev. | Median |
|---|---|---|---|
| 186-plex | 9.86 | 0.47 | 9.84 |
| 368-plex | 10.01 | 0.82 | 10.10 |
| 738-plex | 9.94 | 0.43 | 9.97 |
| 1013-plex | 9.98 | 0.67 | 10.10 |

The results demonstrate that there was no degradation in performance in carrying out multiplex amplifications at very high levels of complexity.

7.6 Example 6

Multiplex PCR Amplifications can be Carried Out in the Presence of Uracil N-Glycosylase (UNG)

A method for preventing "carry over" contamination in PCR includes the use of dUTP in place of dTTP in the PCR mixture, followed by treatment of all subsequent PCR mixtures with uracil N-glycosylase (UNG) (U.S. Pat. No. 5,035,996). The experiment in this Example was performed in order to evaluate the effect of the presence of UNG on the efficiency of multiplex amplifications.

A first 186-plex amplification (UNG(−)) was carried out as described in Example 5, but using TAQMAN® Universal Master Mix, No AMPERASE® UNG (Cat. #4324018), instead of Universal Master Mix (Cat. #4304437). The multiplex amplification was extended for 14 cycles, instead of 10 cycles, as in Example 5. The samples were chilled on ice after the amplification, and then subjected to single-plex PCR as described in Example 5.

Another 186-plex amplification (UNG(+)) was carried out as described in Example 5, but using Universal Master Mix (Cat. #4304437) (with UNG), except that the 186-plex amplification was extended through 14 cycles, and the samples were chilled on ice for 4 hours. The samples were subjected to single-plex PCR as described in Example 5.

For each of these two protocols, corresponding control multiplex amplifications were set up, but these control reactions were not subjected to thermal cycling. The ΔCt value for the single-plex amplification from the "UNG(−)" protocol and from the "UNG(+)" protocol were obtained and plotted in a bar graph (FIG. 8). The following table summarizes the results of the two protocols:

| | Avg. ΔCt | Std. Dev. | Median |
|---|---|---|---|
| UNG(−) | 14.13 | 0.62 | 14.08 |
| UNG(+) | 13.94 | 0.81 | 13.96 |

In this Example, the effect of the presence of UNG in a multiplex amplification, carried out in a procedure similar to that described in Example 5, was evaluated. The presence of UNG in the multiplex amplification had essentially no affect on the efficiency of amplification in the single-plex amplification step as compared to the UNG(−) sample.

7.7 Example 7

Effect of Increased Cycles of Multiplex Amplification

In Example 5, the multiplex amplification was carried out for 10 cycles. In the present Example, multiplex amplifications were carried out for 10, 12 and 14 cycles. Higher cycle numbers can increase the concentration of the amplification product, which allows a greater number of downstream assays, such as a greater number of single-plex amplifications, to be performed.

Three 186-plex amplifications were carried out as described in Example 5, using Universal Master Mix (Cat. #4324018) (with no AmpErase® UNG), and the multiplex amplification was extended through 10, 12 or 14 amplification cycles. ΔCt values for each the three protocols is shown in FIG. 9 and summarized in the following table.

| Cycles | Avg. ΔCt value | Std. Dev. | Median |
|---|---|---|---|
| 10 | 9.99 | 0.59 | 9.92 |
| 12 | 11.80 | 0.56 | 11.78 |
| 14 | 14.13 | 0.60 | 14.08 |

The average ΔCt value increased as the number of thermal cycles increased. The standard deviations were essentially unchanged. These results indicate that there is no decrease in performance in going from 10 to 14 cycles. If amplifications are 100% efficient, then the ΔCt between amplified and "mock" reactions will be 10 with 10 cycles of amplification, 12 with 12 cycles, and 14 with 14 cycles. In this Example, the average ΔCt values approximated 10 (9.99), 12 (11.8), and 14 (14.13), respectively.

7.8 Example 8

Quantification of mRNA in Human Plasma by RT-PCR Multiplex Amplification

The detection of circulating RNA in plasma can allow for early detection of disease states such as cancer, coronary and autoimmune dysfunctions and can also be used to monitor the success of drug treatment regimes by following gene expression.

This Example demonstrates generation of cDNA from a sample of mRNA followed by multiplex PCR amplification of the cDNA in the presence of a plurality of selected PCR primers within a single reaction mixture, with subsequent single-plex real-time PCR in the presence of each of the selected PCR primers.

Whole blood was obtained from a healthy donor and spun at 2000×g for 20 min. The cell-free supernatant was decanted and filtered through a 0.2 μm filter. The recovery (volume approximately 10 ml) was about 50% of the whole blood volume. RNA was extracted and subjected to ethanol precipitation. The RNA pellet was re-suspended in 200 μl of TE buffer.

Equal volumes (10 μl each) of 108 selected 20× Assays-on-Demand Gene Expression Products were pooled and dried down using a SpeedVac® concentrator (Thermo Savant, Holbrook, N.Y.). The residue was re-suspended in deionized water to yield a primer concentration of 180 nM for each primer. The 108 Assay-on-Demand primers corresponded to solid tissue and leukocyte specific amplicons, examples of which included: pinin, hexokinase-1, VEGFβ, PRKCB1, LGALS3BP, cyclophilin A, GAS2L1, DDX1, TERT, BMPR2, LANCL1, and CCL5.

The reverse transcriptase (RT) and multiplex amplification incubation contained the following: 125 µl of 2× Universal Master Mix for one-step RT-PCR (TaqMan® One Step Master Mix Reagents Kit, No AmpErase® UNG, Cat. #4309169); 12.5 µl AmpliTaq Gold (5 U/µl=5 Units extra per 20 µl multiplex amplification volume); 6.25 µl of reverse transcriptase/ RNase inhibitor; 106.25 µl plasma RNA (240 ng); and 62.5 µl of the pooled and re-suspended 108 Assay-on-Demand Products. The final volume was 250 µl (240 ng plasma RNA), and 50 µl was aliquoted into separate wells of a 96-well plate.

The reverse transcription reaction was carried out for 30 min at 48° C., followed by denaturation for 10 min at 95° C. The multiplex amplification was carried out for a total of 14 cycles (each cycle: 15 sec at 95° C.; 4 min. anneal/extend at 60° C.). These reactions were carried out on an ABI Prism® 7700 instrument.

In "mock" multiplex amplifications which included the reverse transcription reaction, but in which the 14 cycles of PCR multiplex amplification were omitted, no signal due to specific amplicons could be detected. The following table summarizes the results for selected targets:

| Target | Ct |
|---|---|
| 18S | 20.36(0.03) |
| Pinin | 32.83(0.54) |
| Hexokinase-1 | 32.10(0.62) |
| VEGFβ | 34.20(0.38) |

The results indicate that DNA obtained from reverse transcription of human plasma RNA, and subjected to multiplex amplification in the presence of a plurality of primer pairs, can subsequently be single-plex amplified using the same primer pairs without optimization.

Unless mentioned otherwise the techniques employed or contemplated herein are standard methodologies well known to one of ordinary skill in the art. The materials, methods and examples are illustrative only and not limiting.

While the foregoing has presented specific embodiments of the present invention, it is to be understood that these embodiments have been presented by way of example only. It is expected that others will perceive and practice variations which, though differing from the foregoing do not depart form the spirit and scope of the invention as described and claimed herein. All patent applications, patents, and literature references cited in this specification are hereby incorporated by reference in their entirety.

What is claimed is:

1. A method for analyzing a sample or plurality of samples for the presence of one or more polynucleotide sequences of interest, comprising:
   (i) amplifying at least one of said polynucleotides of interest in the presence of:
      (a) a plurality of different amplification primer pairs suitable for amplifying said polynucleotide sequences of interest; and
      (b) a plurality of oligonucleotide probes, wherein each of said plurality of oligonucleotide probes is complementary to a region of a different polynucleotide sequence of interest amplified by said plurality of primer pairs and comprises a label suitable for monitoring amplification as a function of time; and
   (ii) amplifying the products of said step (i) by dividing said products of step (i) into a plurality of aliquots and performing real-time polymerase chain reaction (PCR) on at least one of said aliquots in the presence of:
      (a) at least one of said primer pairs used in step (i); and
      (b) at least one of said oligonucleotide probes used in step (i) wherein said oligonucleotide probe in step (ii) is complementary to a region of a polynucleotide sequence of interest amplified by said primer pair in step (ii), wherein said step (i) amplifying is carried out for less than 40 cycles.

2. The method of claim 1 in which the amplification of step (i) is further carried out in the presence of a reverse transcriptase such that the polymerase chain reaction is reverse-transcription polymerase chain reaction and wherein the one or more polynucleotide sequences is obtained from mRNA derived from the sample.

3. The method of claim 1 in which the one or more polynucleotide sequences comprise a cDNA library.

4. The method of claim 1 in which the polymerase chain reaction of step (i) is carried out for a number of cycles such that the amplification remains in the linear range.

5. The method of claim 1 in which the amplification in step (i) is achieved with a thermostable DNA polymerase.

6. The method of claim 1 in which the label is a fluorophore.

7. The method of claim 1 in which said plurality of oligonucleotide probes is selected from the group consisting of 5'-exonuclease probes, stem-loop beacon probes and stemless beacon probes.

8. The method of claim 1 in which an observed efficiency of amplification is greater than 70%.

9. The method of claim 1 in which an observed efficiency of amplification is greater than 90%.

10. The method of claim 1 in which the amplification is carried out in the presence of uracil N-glycosylase.

11. The method of claim 1 in which the amplifying of step (i) comprises fewer than fifteen PCR cycles.

12. The method of claim 1, wherein said less than 40 cycles is a number of cycles suitable to keep said amplification reaction within the exponential or linear phase.

* * * * *

UNITED STATES PATENT AND TRADEMARK OFFICE
CERTIFICATE OF CORRECTION

| | | |
|---|---|---|
| PATENT NO. | : 8,323,897 B2 | Page 1 of 1 |
| APPLICATION NO. | : 10/723520 | |
| DATED | : December 4, 2012 | |
| INVENTOR(S) | : Andersen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 638 days.

Signed and Sealed this
Sixteenth Day of December, 2014

Michelle K. Lee
*Deputy Director of the United States Patent and Trademark Office*